(12) United States Patent
Watkins et al.

(10) Patent No.: US 10,898,479 B2
(45) Date of Patent: Jan. 26, 2021

(54) DIHYDROETORPHINE FOR THE PROVISION OF PAIN RELIEF AND ANAESTHESIA

(71) Applicant: EURO-CELTIQUE S.A., Luxembourg (LU)

(72) Inventors: John Watkins, Cambridge (GB); Alexander Oksche, Cambridge (GB); Kevin Smith, Cambridge (GB); Heikki Mansikka, Cambridge (GB); Paul Bailey, Cambridge (GB)

(73) Assignee: Euro-Celtique S.A., Luxembourg (LU)

( * ) Notice: Subject to any disclaimer, the term of this patent is extended or adjusted under 35 U.S.C. 154(b) by 497 days.

(21) Appl. No.: 14/894,775

(22) PCT Filed: May 30, 2014

(86) PCT No.: PCT/GB2014/000206
§ 371 (c)(1),
(2) Date: Nov. 30, 2015

(87) PCT Pub. No.: WO2014/191710
PCT Pub. Date: Dec. 4, 2014

(65) Prior Publication Data
US 2016/0106736 A1    Apr. 21, 2016

(30) Foreign Application Priority Data

May 30, 2013   (GB) .................................. 1309654.0

(51) Int. Cl.
*A61K 31/485*    (2006.01)
*A61K 45/06*    (2006.01)
*C07D 489/12*    (2006.01)

(52) U.S. Cl.
CPC ............ *A61K 31/485* (2013.01); *A61K 45/06* (2013.01); *C07D 489/12* (2013.01)

(58) Field of Classification Search
CPC .................................................. A61K 31/485
See application file for complete search history.

(56) References Cited

U.S. PATENT DOCUMENTS

| | | | |
|---|---|---|---|
| 4,891,377 A | 1/1990 | Shipman, Jr. et al. |
| 5,271,940 A | 12/1993 | Cleary et al. |
| 5,624,932 A | 4/1997 | Qin et al. |
| 5,849,915 A | 12/1998 | Kim et al. |
| 5,876,746 A | 3/1999 | Jona et al. |
| 6,312,716 B1 | 11/2001 | Midha et al. |
| 6,372,252 B1 | 4/2002 | Blume et al. |
| 6,743,441 B2 | 6/2004 | Sanders et al. |
| 6,770,295 B1 | 8/2004 | Kreilgård et al. |
| D576,282 S | 9/2008 | Yanaki |
| 7,718,188 B2 | 5/2010 | Ito et al. |
| D625,017 S | 10/2010 | Iwahashi et al. |
| 8,071,125 B2 | 12/2011 | Wang et al. |
| 9,206,190 B2 | 12/2015 | Whitelock et al. |
| 9,481,681 B2 | 11/2016 | Whitelock et al. |
| 2002/0010127 A1 | 1/2002 | Oshlack et al. |
| 2003/0064099 A1 | 4/2003 | Oshlack et al. |
| 2003/0068392 A1 | 4/2003 | Sackler |
| 2003/0148941 A1 | 8/2003 | Crain et al. |
| 2003/0191147 A1 | 10/2003 | Sherman et al. |
| 2004/0024005 A1 | 2/2004 | Whistler et al. |
| 2004/0033255 A1 | 2/2004 | Baker et al. |
| 2004/0208917 A1 | 10/2004 | Fischer et al. |
| 2004/0242616 A1 | 12/2004 | Jackson et al. |
| 2005/0002997 A1 | 1/2005 | Howard et al. |
| 2005/0101622 A1 | 5/2005 | Crain et al. |
| 2005/0113365 A1 | 5/2005 | Lundeen |
| 2006/0039960 A1 | 2/2006 | Cordes et al. |
| 2006/0111381 A1 | 5/2006 | Jackson et al. |
| 2006/0111382 A1 | 5/2006 | Shafer et al. |
| 2006/0177381 A1 | 8/2006 | Brooks-Korn |
| 2007/0037891 A1 | 2/2007 | Esfand et al. |
| 2007/0128263 A1 | 6/2007 | Gargiulo et al. |
| 2008/0039775 A1 | 2/2008 | Ameri et al. |
| 2010/0150993 A1 | 6/2010 | Theobald et al. |
| 2011/0027345 A1 | 2/2011 | Wang et al. |
| 2012/0010231 A1 | 1/2012 | Whitelock et al. |
| 2012/0082714 A1 | 4/2012 | Bracht et al. |
| 2017/0267687 A1 | 9/2017 | Whitelock et al. |

FOREIGN PATENT DOCUMENTS

| | | |
|---|---|---|
| CA | 2 670 290 C | 5/2016 |
| CN | 1676130 | 10/2005 |
| CN | 1957918 | 5/2007 |
| EP | 0 418 591 A2 | 3/1991 |
| EP | 0 680 754 B1 | 9/1998 |
| EP | 1 174 137 B1 | 10/2006 |
| EP | 1 439 179 B1 | 3/2008 |
| EP | 2 286 802 A1 | 2/2011 |
| EP | 2 286 814 A1 | 2/2011 |
| EP | 2 298 277 A1 | 3/2011 |
| GB | 925723 | 5/1963 |
| GB | 937214 | 9/1963 |
| JP | 59-184182 | 10/1984 |
| JP | 62-153214 | 7/1987 |
| JP | 62-281815 | 12/1987 |
| JP | 63-201119 | 8/1988 |
| JP | 3-163083 | 7/1991 |
| JP | 8-504189 | 5/1996 |
| JP | 10-231248 | 9/1998 |

(Continued)

OTHER PUBLICATIONS

Ohmori et al. (CNS Drug Reviews vol. 8, No. 4, pp. 391-404).*

(Continued)

*Primary Examiner* — Jeffrey S Lundgren
*Assistant Examiner* — Chris E Simmons
(74) *Attorney, Agent, or Firm* — Sterne, Kessler, Goldstein & Fox P.L.L.C.

(57) ABSTRACT

The present invention provides a method of providing pain relief in a human subject in need thereof comprising administering (R)-dihydroetorphine to said subject, wherein said (R)-dihydroetorphine is administered in a dose of at least 0.01 µg/kg, preferably at least 0.05 µg/kg, and the level of respiratory depression in said subject is 65 or less % relative to the baseline level pre-administration of (R)-dihydroetorphine.

32 Claims, 11 Drawing Sheets

(56) References Cited

FOREIGN PATENT DOCUMENTS

| WO | WO 94/06426 A1 | 3/1994 |
|---|---|---|
| WO | WO 97/14438 | 4/1997 |
| WO | WO 00/01377 | 1/2000 |
| WO | WO 00/51592 A1 | 9/2000 |
| WO | WO 02/05647 A1 | 1/2002 |
| WO | WO 03/070191 A1 | 8/2003 |
| WO | WO 2004/017941 A2 | 3/2004 |
| WO | WO 2004/064839 A1 | 8/2004 |
| WO | WO 2006/110642 A2 | 10/2006 |
| WO | WO 2007/011125 A1 | 1/2007 |
| WO | WO 2007/022535 A2 | 2/2007 |
| WO | WO 2007/052308 A2 | 5/2007 |
| WO | WO 2007/059445 A2 | 5/2007 |
| WO | WO 2008/061625 A2 | 5/2008 |
| WO | WO 2008/083149 A1 | 7/2008 |
| WO | WO 2008/109156 A2 | 9/2008 |
| WO | WO 2009/088142 A1 | 7/2009 |
| WO | WO 2010/067101 A1 | 6/2010 |

OTHER PUBLICATIONS

Bretz et al. Stat Med. (Mar. 30, 2010); 29(0):731-742. doi:10.1002/sim.3802. (Year: 2010).*
Bian, C.F., et al., "Relationship between dihydroetorphine and cholinergic system in the inhibition of respiration and heart rate," *NIDA Research Monograph* 75:516-519, National Institute on Drug Abuse, United States (1986).
Boeckmann, A.J., et al., "NONMEM Users Guide—Part VIII," nonmem.icorplc.com, accessed at https://nonmem.iconplc.com/nonmem720/guides, accessed on Feb. 24, 2015. 638 pages (Apr. 2011).
Dahan, A., et al., "The influence of oxygen on the ventilatory response to carbon dioxide in man," *J. Physiol.* 428:485-499, Cambridge Univ. Press, England (1990).
Dahan, A., et al., "Comparison of the respiratory effects of intravenous buprenorphine and fentanyl in humans and rats," *British Journal of Anaesthesia* 94(6):825-834, The Board of Management and Trustees of the British Journal of Anaesthesia, England (2005).
Dahan, A., et al., "Plasticity of central chemoreceptors: effect of bilateral carotid body resection on central $CO_2$ sensitivity," *PLoS Medicine* 4(7):e239:1195-1203, Public Library of Science, United States (2007).
Foley, K.M., "Pain," in *Cecil Textbook of Medicine*, 20$^{th}$ edition, Bennett, J.C. and Plum, F., eds., pp. 100-107, W.B. Saunders Company, United States (1996).
Gao, Y., et al., "The analgesic effect of dihydroetorphine in percutaneous hepatic artery chemoembolization therapy for liver cancer," *Journal of Interventional Radiology* 22(11):904-907, China (Nov. 2013).
Huang, M., et al., "Dihydroetorphine, a potent opioid with low dependent potential," *Regulatory Peptides* 53(Supplement 1):S8I-S82, Elsevier Science B.V., Netherlands (1994).
Kamei, J., et al., "Antitussive effect of dihydroetorphine in mice," *Eur. J. Pharmacol.* 260(2-3):257-259, Elsevier Science B.V., Netherlands (1994).
Li, E. and Weng, L., "Influence of dihydroetorphine hydrochloride and tramadol on labor pain and umbilical blood gas," *Chinese Journal of Obstetrics and Gynecology* 30(6):345-348, China (1995).
Liu, F., et al., "Determination of dihydroetorphine in biological fluids by gas chromatography-mass spectrometry using selected-ion monitoring," *J. Chromatogr. B. Biomed. Appl.* 679(1-2):113-118, Elsevier Science B.V., Netherlands (1996).
Martin. T.J., et al., "Anti-alloclynic actions of intravenous opioids in the nerve injured rat: potential utility of heroin and dihydroetorphine against neuropathic pain," *Eur. J. Pharmacol.* 357(1):25-32, Elsevier Science B.V., Netherlands (1998).
Ohmori, S. and Morimoto, Y., "Dihydroetorphine: a potent analgesic: pharmacology, toxicology, pharmacokinetics, and clinical effects," *CNS Drug Rev.* 8(4):391-404, Neva Press, Inc., United States (2002).
Wikipedia, "Dihydroetorphine" Wikipedia.com, accessed at http://en.wikipedia.org/wiki/Dihydroetorphie, accessed on May 12, 2013, 2 pages.
Yassen, A., et al., "Mechanism-based PK/PD modeling of the respiratory depressant effect of buprenorphine and fentanyl in healthy volunteers," *Clin. Pharmacol. Thor.* 81(1):50-58, Wiley, United States (2007).
International Preliminary Report on Patentability for International Application No. PCT/GB2014/000206, International Bureau of WIPO, Geneva, Switzerland, dated Dec. 1, 2015, 8 pages.
International Search Report for International Application No. PCT/GB2014/000206, European Patent Office, Rijswijk, Netherlands, dated Sep. 29, 2014, 4 pages.
Bentley, K.W., et al., "Novel analgesics and molecular rearrangements in the morphine-thebaine group. III. Alcohols of the 6,14-endo-ethenotetrahydrooripavine series and derived analogs of N-allylnormorphine and -norcodeine," *J. Am. Chem. Soc.* 89(13):3281-3292, American Chemical Society, United States (1967).
Bentley, K.W., et al., "Novel analgesics and molecular rearrangements in the morphine-thebaine group. IV. Acid-catalyzed rearrangements of alcohols of the 6,14-endo-ethenotetrahydrothebaine series," *J. Am. Chem. Soc.* 89(13):3293-3303, American Chemical Society, United States (1967).
Casy, A.F. and Parfitt, R.T., "Diels-Alder Adducts of Thebaine," in *Opioid Analgesics: Chemistry and Receptors*, pp. 69-73, Plenum Press, United States (1986).
Chuanjin, C., et al., "To Improve the Synthesis of Dihydroetorphine," *Acta Academiae Medicinae Shanghai* 19(3):223-224, Shanghai Medical University, China (1992)
English language translation of Chuanjin, C., et at., "To Improve the Synthesis of Dihydroetorphine," *Acta Academiae Medicinae Shanghai* 19(3):223-224, Shanghai Medical University, China (1992).
Hutchins, C.W. and Rappaport, H., "Analgesics of the Orvinol Type. 19-Deoxy and 6,20-Epoxy Derivates," *J. Med. Chem.* 27:521-527, American Chemical Society, United States (1984).
Li, Y-g. and Xu, C-x., "Amelioration of Demethylation to Synthetic Etorfy and Hydroetorfy," *J. Guangxi Univ. (Nat. Sci. Ed.)* 29(3):265-268, Guangxi University, China (2004).
Liu, H., et al., "Synthesis, Crystal Structural and Pharmacological Study of N-Cyclopropylmethyl-7α-[(R)-1-hydroxyl-1-methyl-3-(thien-2-yl)propyl]-6,14-endoethanotetrahydronooripavine," *Acta Chim. Slov.* 52:80-85, Slovenian Chemical Society, Slovenia (2005).
Lewis, J., "Ring C-bridged derivatives of thebaine and oripavine," *Adv. Biochem. Psychopharmacol.* 8(0):123-136, Raven Press, United States (1974).
Ma, X., et al., "Synthesis of the Highly Effective Analgesic Etorphine," *Fine Chemical Industry* 13(1): 12-15, Dalian Institute of Light Industry, China (1996).
Ohmori, S., et al., "A protective effect against undesirable increase of dihydroetorphine permeation through damaged skin by using pressure-sensitive adhesive tape with an ethylene-vinyl acetate co-polymer membrane," *Biol. Pharm. Bull.* 24(1):78-83, Pharmaceutical Society of Japan, Japan (2001).
Qin, B-Y., "Advances in Dihydroetorphine: From Analgesia to Detoxification," *Chin. Bull. Drug. Depend.* 5(4):1-5, China Academic Journal Electronic Publishing House, China (1991).
English language translation of Qin, B-Y., "Advances in Dihydroetorphine: From Analgesia to Detoxification," *Chin. Bull. Drug. Depend.* 5(4):1-5, China Academic Journal Electronic Publishing House, China (1991).
Wang, N-S., et al., "Dihydroetorphine in Conditioned Place Preference," *Chin. Bull. Drug Depend.* 2(4):271-273, China Academic Journal Electronic Publishing House, China (1993).
English language translation of Wang, N-S., et al., "Dihydroetorphine in Conditioned Place Preference," *Chin. Bull. Drug Depend.* 2(4):271-273, China Academic Journal Electronic Publishing House, China (1993).
Xifa, S. and Li, C., "An Adjuvant Response of Dihydroetorphine in General Anesthesia and Effect on Respiration and Circulation," *Chin. Pharmacist* 5(8):490-491, China Academic Journal Electronic Publishing House, China (2002).

(56) References Cited

OTHER PUBLICATIONS

English language translation of Xifa, S. and Li, C., "An Adjuvant Response of Dihydroetorphine in General Anesthesia and Effect on Respiration and Circulation," *Chin. Pharmacist* 5(8):490-491, China Academic Journal Electronic Publishing House, China (2002).

Miao, Z.-C., et al., "$^1$H and $^{13}$C NMR and Stereochemistry of the Analgesic Dihydroetophine," *Chin. J. Org. Chem.* 9(4):347-352, Chinese Chemical Society, China (1989).

English language translation of Miao, Z.-C., et al., "$^1$H and $^{13}$C NMR and Stereochemistry of the Analgesic Dihydroetophine," *Chin. J. Org. Chem.* 9(4):347-352, Chinese Chemical Society, China (1989).

Xu, J.-P., et al., "Effect of dihydroetorphine, ohmefentanyl and etonitazene on immune function in mice," *Chin. J. Pharmacol. Toxicol.* 7(4):290-293, China Academic Journal Electronic Publishing House, China (1993).

English language translation of Xu, J.-P., et al., "Effect of dihydroetorphine, ohmefentanyl and etonitazene on immune function in mice," *Chin. J. Pharmacol. Toxicol.* 7(4):290-293, China Academic Journal Electronic Publishing House (1993).

Miao, H., et al., "The Analgesic Effect of Combined Administration of Dihydroetorphine and Tramadol Mice," *Zhongguo Yaolixue Yu Dulixue Zazhi* 7(4):285, China Academic Journal Electronic Publishing House, China (1993).

English language translation of Miao, H., et al., "The Analgesic Effect of Combined Administration of Dihydroetorphine and Tramadol Mice," *Zhongguo Yaolixue Yu Dulixue Zazhi* 7(4):285, China Academic Journal Electronic Publishing House, China (1993).

English language abstract of JP 62-153214, espacenet database, Worldwide, published Jul. 18, 1987.

English language abstract of JP 62-281815, espacenet database, Worldwide, published Dec. 7, 1987.

English language abstract of JP 63-201119, espacenet database, Worldwide, published Aug. 19, 1988.

English language abstract of JP 10-231248, espacenet database, Worldwide, published Sep. 2, 1998.

International Search Report dated Apr. 28, 2010 for International application No. PCT/GB2009/051655 by the European Patent Office, Rijswijk.

International Preliminary Report on Patentability and the Written Opinion dated Jun. 14, 2011 for International application No. PCT/GB2009/051655 by the International Bureau of WIPO, Geneva.

Bentley, K.W., et al., "Novel Analgesics and Molecular Rearrangements in the Morphine-Thebaine Group. II. Alcohols Derived from 6,14-endo-Etheno- and 6,14-endo-Ethanotetrahydrothebaine," *Journal of the American Chemical Society* 89(13): 3273-3280, American Chemical Society, United States (1967).

Bentley, K.W., et al., "Novel Analgesics and Molecular Rearrangements in the Morphine-Thebaine Group. I. Ketones Derived from 6,14-endo-Ethenotetrahydrothebaine," *J. Am. Chem. Soc.* 89(13):3267-3273, American Chemical Society, United States (1967).

Coop, A., et al., "Methylation of Enolates of Thevione and some Analogues," *Tetrahedron* 51(35): 9681-9698, Elsevier Science Ltd, Great Britain (1995).

Marton, J., et al., "Herstellung von 6,14-Ethenomorphinan-Derivaten," *Monatschefte für Chemie* 125: 1229-1239, Springer-Verlag, Austria (1994).

Park, H., et al., "A highly selective κ-opioid receptor agonist with low addictive potential and dependence liability," *Bioorganic & Medicinal Chemistry Letters* 16: 3609-3613, Elsevier Ltd., Great Britain (2006).

Aceto, M.D., et al., "Dihydroetorphine: physical dependence and stereotype 2 after continuous infusion in the rat," *European Journal of Pharmacology* 387:31-37, Elsevier Science B.V., Netherlands (2000).

Aceto, M., et al., "Etorphines: μ-opiod receptor-selective antinociception and low physical dependence capacity," *European Journal of Pharmacology* 338: 215-223, Elsevier Science B.V., Netherlands (1997).

Beardsley P., and Harris, L.S.., "Evaluation of the discriminative stimulus and reinforcing effects of dihydroetorphine," *Drug and Alcohol Dependence* 48:77-84, Elsevier Science Ireland Ltd., Ireland (1997).

Chen, X.-P., et al., "Transdermal Permeation of Dihydro Etorphine Hydrochloride-Influence pH, Concentration and Surfactants on in vitro Permeation," *Journal of Chinese Pharmaceutical Sciences* 4(4):187-192, Editorial Office of Journal of Chinese Pharmaceutical Sciences, Beijing, China (1995).

Rennison, D., et al., "Formic Acid Catalysed Rearrangement of 5β-Methyldihydrothevinols (=-3,6-Dimethoxy-5,17-dimethyl-4,5-epoxy-6,14-ethanomorphinan-7-methanols): Synthesis of New Doubly Bridged Morphinan Derivatives," *Chemistry & Biodiversity* 2(2):215-220, Verlag Helvetica Chimica Acta AG, Zürich, Switzerland (2005).

Biyashev, D., et al., "Biochemical characterisation of newly developed (β-etorphine and β-dihydroetorphine derivatives," *European Journal of Pharmacology* 442:23-27 Elsevier Science B.V., Netherlands (2002).

Cao, Y.X., et al., "A survey of 185 dihydroetorphine hydrochloride abusers," *Chin. Bull. Drug Depend.* 4(1):21-24, Gai Suo, Beijing, China (1995).

Chen, J., et al., "Application and comparison of three methods in evaluating the potency of psychological dependence," *Chinese Pharmacological Bulletin* 12(3):235-238, China Academic Journal Electronic Publishing House, China (1996).

Chen, X., et al., "Studies on transdermal delivery system of dihydroetorphine hydrochloride," *Acta. Pharm. Sin.* 31(10):770-774, China Academic Journal Electronic Publishing House, China (1996).

English language translation of Chen, X., et al., "Studies on transdermal delivery system of dihydroetorphine hydrochloride," *Acta. Pharm. Sin.* 31(10):770-774, China Academic Journal Electronic Publishing House, China (1996), 7 pages.

Choe, C.H., et al., "Sedative tolerance accompanies tolerance to the analgesic effects of fentanyl in infant rats," *Pediatric Research* 47:727-735, International Pediatric Research Foundation, Inc., United States (2000).

English language translation of Chinese package insert "Dihydroetorphine Hydrochloride Sublingual Tablets," Beijing Sihuan Science and Technology Co. Ltd., accessed at www.sihuan.com.cn, accessed on Mar. 5, 2009.

Commission on Narcotic Drugs, Report on the forty-second Session 1999, Supplement No. 8, pp. 1-97, Economic and Social Council, United Nations, New York (2000).

English language translation of Li, E., et al., "Influence of dihydroetorphine hydrochloride and tramadol on labor pain and umbilical blood gas," *Chinese Journal of Obstetrics and Gynecology* 30:345-348, Zhonghua Yi Xue Hi, Peking, China (1995), 3 pages.

Crain, S., et al., "Etorphine Elicits Unique Inhibitory-Agonist and Excitatory-Antagonist Actions at Opioid Receptors on Sensory Neurons: New Rationale for Improved Clinical Analgesia and Treatment of Opiate Addiction," *National Institute on Drug Abuse, Research Monograph Series* 147: 234-268, U.S. Department of Health and Human Services, NIH, United States (1995).

Franz, T.J., "Percutaneous absorption on the relevance of in vitro data," *Journal of Investigative Dermatology* 6 (3):190-195, Williams and Wilkins Co., United States (1975).

English translation of Ge, Y., et al:, "Clinical assessment of physical dependence potential of dihydroetorphine hydrochloride (DHE)," *Acta. Pharm. Sinica.* 29 (4):256-260, Shanghai Ke Xue Ji Shu Chu Ban She, Shanghai, China (1994), 6 pages.

Gerak, LR., et al., "Discriminative stimulus and antinociceptive effects of dihydroetorphine in rhesus monkeys," *Psychopharm.* 166:351-359, Springer-Verlag, Germany (2003).

English translation of Chen, J., et al., "Application and comparison three methods in evaluating the potency of psychological dependence," *Chinese Pharmacological Bulletin* 12(3):235-238, China Academic Journal Electronic Publishing House, China (1996), 7 pages.

(56) References Cited

OTHER PUBLICATIONS

Greaves, P., "Histopathology of Preclinical Studies," in *Interpretation and Relevance in Drug Safety Evaluation*, 3rd Edition, pp. 126-127, Elsevier Science B.V., Netherlands (2007).
English language translation of Wang, A., et al., "Effect of dihydroetorphine on mice parturition," *Chin. J. Obstet. Gynecol.* 31(5): 299-301 Zhonghua Yi Xue Hi, Peking, China (1996), 5 pages.
Guo, Q., et al., "Effect of vehicle pH, drug concentration and Azone on the snake skin permeation of dihydroetorphine hydrochloride," *Chin. Pharm. J.* 32(6):349-352, Pharmaceutical Society of Republic of China, Taipei, Taiwan (1997).
English language translation of Guo, Q., et al., "Effect of vehicle pH, drug concentration and Azone on the snake skin permeation of dihydroetorphine hydrochloride," *Chin. Pharm. J.* 32(6): 349-352, Pharmaceutical Society of Republic of China, Taipei, Taiwan (1997), 6 pages.
He, J., et al., "Reports of 103 cases drug addiction by dihydroetorphine," *Journal of Comprehensive Clin. Med* 12(6):299, American Society of Comprehensive Medicine, United States (1996).
English language translation of He, J., et al., "Reports of 103 cases drug addiction by dihydroetorphine," *Journal of Comprehensive Clin. Med.* 12(6):299, American Society of Comprehensive Medicine, United States (1996), 2 pages.
Higuchi, T., "Rate of Release of Medicaments from Ointment Bases Containing Drugs in Suspension," *Journal of Pharmaceutical Sciences* 50:874-875, American Pharmaceutical Association, United States (1961).
Zheng, J., et al., "Psychological dependence potential of dihydroetorphine hydrochloride," *Chin. Bull. Drug Depend.* 4(2):65-69, Gai Suo, Beijing, China (1995).
Huang, C., et al., "Clinical use of dihydroetorphine (M99) in department of digestive diseases," *Acta. Phys. Sin.* 2:25, Allerton Press, United States (1985).
English language translation of Huang, C., et al., "Clinical use of dihydroetorphine (M99) in department of digestive diseases," *Acta. Phys. Sin.* 2:25, Allerton Press, United States (1985), 1 page.
Huang, M., et al., "Pharmacodynamics and Pharmacokinetics of Dihydroetorphine Hydrochloride Administered Sublingually in Mice and Rats," *Acta Pharmacologica Sinica* 9(4):308-312, Shanghai Ke Xue Ji Shu Chu Ban She, Shanghai, China (1988).
Huang, M., et al., "Analgesic and other CNS depressive effects of dihydroetorphine," *Acta Pharmacologica Sinica* 3(1):9-13, Shanghai Ke Xue Ji Shu Chu Ban She, Shanghai, China (1982).
English language translation of Huang, M., et al., "Analgesic and other CNS depressive effects of dihydroetorphine," *Acta Pharmacologica Sinica* 3(1):9-13, Shanghai Ke Xue Ji Shu Chu Ban She, Shanghai, China (1982), 7 pages.
Huang, M., et al., "Physical dependence of dihydroetorphine in mice and monkeys," *Acta Pharmacologica Sinica* 3(2):81-84, Shanghai Ke Xue Ji Shu Chu Ban She, Shanghai, China (1982).
English language translation of Huang, M., et al., "Physical dependence of dihydroetorphine in mice and monkeys," *Acta Pharmacologica Sinica* 3(2):81-84, Shanghai Ke Xue Ji Shu Chu Ban She, Shanghai, China (1982), 3 pages.
Chinese package insert "Dihydroetorphine Hydrochloride Injection Instructions," chinapharm.com.cn, accessed at www.chinapharm.com.cn, accessed on Mar. 3, 2009, 4 pages.
English language translation of Chinese package insert "Dihydroetorphine Hydrochloride Injection Instructions," chinapharm.com.cn, accessed at www.chinapharm.com.cn, accessed on Mar. 3, 2009, 6 pages.
Kamei, J., et al, "Antinociceptive effect of dihydroetorphine in diabetic mice," *European Journal of Pharmacology* 275:109-113, Elsevier Science B.V., Netherlands (1995).
Kamei, J., et al., "Agonist and antagonist properties of dihydroetorphine for μ-opioid receptors in mice," *Neuroscience Letters* 215:87-90, Elsevier Science Ireland Ltd., Ireland (1996).

Katsumata S., et al., "Pharmacological study of dihydroetorphine in cloned μ-, δ-, and κ-opioid receptors," *European Journal of Pharmacology, Molecular Pharmacology Section* 291:367-373, Elsevier Science B.V., Netherlands (1995).
Li, E., et al., " Influence of dihydroetorphine hydrochloride and tramadol on labor pain and umbilical blood gas," *Chinese Journal of Obstetrics and Gynecology* 30:345-348, Zhonghua Yi Xue Hi, Beijing, China (1995).
Li, J., "Recent Progress in the Research Field of Neuropharmacology in China," *Cell. Mol. Neurobiol.* 28:185-204, Springer Science + Business Media, LLC, United States (2008).
Liu, Z.M., et al., "An epidemiological study on DHE abuse," *Chin. Bull. Drug Depend.* 4(4): 223-231, Gai Suo, Beijing, China (1995).
English language translation of Zheng, J., et al., "Psychological dependence potential of dihydroetorphine hydrochloride," *Chin. Bull. Drug Depend.* 4(2):65-69, Gai Suo, Beijing, China (1995), 9 pages.
Luo, Y., et al., "Monitoring of dihydroetorphine hydrochloride in biological fluid," *Acta Pharmacologica Sinica* 29(9):702-706, China Academic Journal Electronic Publishing House, China (1994).
English language translation of Luo, Y., et al., "Monitoring of dihydroetorphine hydrochloride in biological fluid," *Acta Pharmacologica Sinica* 29(9): 702-706, China Academic Journal Electronic Publishing House, China (1994), 7 pages.
Chen, Y-J. and Chen, C., "Synthesis of deuterium-labelled etorphine and dihydroetorphine," *Journal of Labelled Compounds and Radiopharmaceuticals* 50(13):1143-1147, John Wiley & Sons Ltd., England (2007).
English language translation of Qian, J., et al., "Preliminary evaluation on the clinical application of dihydroetorphine," *Bulletin of the Academy of Military Medical Sciences* 5:527-529, Jun Shi Xue Ke Xue Yuan Yuan Kan Bian Ji Bu, Beijing, China (1983), 4 pages.
Zang, D., "A Survey on the Utilization of Narcotic Analgesic Drugs in General Hospitals of Qingdao," *Chin. J. Drug Depend* 8(3):204-205 and 221, Beijing Da Xue, China (1999).
Ming, X., et al., "Tramadol and dihydroetorphine produce synergistic analgesic effect and postpones acute opiate tolerance in rat," *Acta Physiologica Sinica* 57: 696-704, China Academic Journal Electronic Publishing House, China (2005).
"Notice for the Management of Prescription of Stupefacient and Psychotropic Substances, " Chinese Ministry of Health, 3 pages, China (2005).
Nagatomo, N., et al., "Temperature dependence of early and late currents in human cardiac wild-type and long Q-T ΔKPQ Na+channels," *Am. J.Physiol. 275 (Heart Circ. Physiol. 44)*:H2016-H2024, American Physiological Society, United States (1998).
Niwa, M., et al., "Opioid receptor interaction and adenylyl cyclase inhibition of dihydroetorphine: direct comparison with etorphine," *Life Sciences* 56:395-400, Elsevier Sciences Ltd., England (1995).
Abel, A.M., et al., "The synthesis of buprenorphine intermediates by regioselective microbial N- and O-demethylation reactions using *Cunninghamella echinulata* NRRL 1384," *Enzyme and Microbial Technology* 33(5):743-748, Elsevier Inc., United States (2003).
Ohmori S., et al., "Pharmacokinetic and pharmacodynamic evaluations of a potent analgesic, dihydroetorphine, in hairless rat," *Journal of Pharmacology and Experimental Therapeutics* 296:528-536, The American Society for Pharmacology and Experimental Therapeutics, United States (2001).
Ohmori, S., et al., "Quantitative determination of dihydroetorphine in rat plasma and brain by liquid chromatography-tandem mass spectrometry," *Journal of Chromatography B* 740:253-263, Elsevier Science B.V., Netherlands (2000).
Ohmori, S., et al., "Transdermal delivery of the potent analgesic dihydroetorphine: kinetic analysis of skin permeation and analgesic effect in the hairless rat," *J. Pharm. Pharmacal.* 52:1437-1449, American Scientific Publishers, United States (2000).
Qian, J., et al., "Preliminary evaluation on the clinical application of dihydroetorphine," *Bulletin of the Academy of Military Medical Sciences* 5:527-529, Jun Shi Xue Ke Xue Yuan Yuan Kan Bian Ji Bu, Beijing, China (1983).
Qin, B.-Y., "Advances in Dihydroetorphine: From Analgesia to Detoxification," *Drug Development Research* 39:131-134, Wiley-Liss, Inc., United States (1996).

(56) References Cited

OTHER PUBLICATIONS

English language translation of Ren., B., et al., "Clinical analgesic effect of dihydroetorphine tablet," *New Drugs and Clinical Remedies* 12(5): 299, Zhongguo Xao Xue Hui Shanghai Fen Hui, Shanghai, China (1993).

Ren., B., et al., "Clinical analgesic effect of dihydroetorphine tablet," *New Drugs and Clinical Remedies* 12(5). 299, Zhongguo Xao Xue Hui Shanghai Fen Hui, Shanghai, China (1993).

"Notice to Strengthen the Management of the use of DHE by the SFDA," SFDA, Chinese Food and Drug Administration, 1 page, China, (1999).

English language translation of "Notice to Strengthen the Management of the use of DHE by the SFDA," SFDA, Chinese Food and Drug Administration, 1 page, China (1999).

Chinese package insert, "Dihydroetorphine Hydrochloride Sublingual Tablets," Beijing Sihuan Science and Technology Co. Ltd., accessed at www.sihuan.com.cn, accessed on Mar. 5, 2009, 5 pages.

Chinese package insert, "Dihydroetorphine Hydrochloride Sublingual Tablets," chinapharm.com.cn, accessed at www.chinapharm.com.cn, accessed on Mar. 5, 2009, 3 pages.

Sun, Q., "Anaesthetic Application of the Strong Analgesic Drug Dihydroetorphine," *Acta. Phys. Sin.* 2:26, Zhongguo Yao Xue Hui, Beijing, China (1982).

English language abstract of Sun, Q., "Anaesthetic Application of the Strong Analgesic Drug Dihydroetorphine," *Acta. Phys. Sin.* 2:26, Zhongguo Yao Xue Hui, Beijing, China (1982).

Tokuyama S., et al., "Antinociceptive Effect of Dihydroetorphine Following Various Routes of Administration: a Comparative Study with Morphine," *Biol. Pharm. Bull.* 19:477-479, Pharmaceutical Society of Japan, Japan (1996).

Tokuyama S., el al., "Antinociceptive Effect of Dihydroetorphine and Its Tolerance/Dependence Liability in Mice," *Biol. Pharm. Bull.* 16(8):774-777, Pharmaceutical Society of Japan, Japan (1993).

Tokuyama, S., et al., "A potent mu-opioid receptor agonist, dihydroetorphine, fails to produce the conditioned place preference in mice," *Jpn. J. Pharmacol.* 71:357-360, Japan Pharmacological Society, Japan (1996).

Tokuyama, S., et al., "Physical dependence produced by dihydroetorphine in mice," *Biol. Pharm. Bull.* 17(8): 1056-1059, Pharmaceutical Society of Japan, Japan (1994).

Van Der Linde, H.J., et al., "The effect of changes in core body temperature on the QT interval in beagle dogs: a previously ignored phenomenon, with a method for correction," *British Journal of Pharmacology* 154:1474-1481, Nature Publishing Group, England (2008).

Wang D.-X., et al., "Experimental therapeutic effects of dihydroetorphine in morphine-dependent rats and monkeys," *Chinese Journal of Pharmacology and Toxicology* 6(1):36-40, Zhongguo Yao Li Xue Hui, Beijing, China (1992).

English language translation of Wang D., et al., "Experimental therapeutic effects of dihydroetorphine in morphine dependent rats and monkeys," *Chinese Journal of Pharmacology and Toxicology* 6(1):36-40, Zhongguo Yao Li Xue Hui, Beijing, China (1992), 10 pages.

Wang, A., et al., "Effect of dihydroetorphine on mice parturition," *Chin. J. Obstet. Gynecol.* 31(5):299-301, Zhonghua Yi Xue Hi, Beijing, China (1996).

Wang, C., et al., "An investigation on the situation of utilization of narcotic medications for cancer pain patients," *Chin. J. Drug Depend.* 8:210-213, Beijing Da Xue, Beijing, China (1999).

English language translation of "Notice for the Management of Prescription of Stupefacient and Psychotropic Substances, " Chinese Ministry of Health, 3 pages, China (2005), 4 pages.

Wang, D.-X., et al, "Dihydroetorphine is a μ-Receptor-selective Ligand," *J. Pharm. Pharmacol.* 47:669-673, Pharmaceutical Society of Great Britain, England (1995).

Wang, W., et al., "Psychological dependence potential of dihydroetorphine in Rhesus monkeys," *Chin. Bull. Drug Depend.* 6(1):8-12, Zhong Guo Yao Wu Yi Lai Xing Zo Zhi Bain Ji Bu, China (1997).

Wang, Z., et al., "Analysis of 9 mortal cases caused by dihydroetorphine hydrochloride abuse," *Chin. Bull. Drug Depend.* 3:176-178, Zhong Guo Yao Wu Yi Lai Xing Zo Zhi Bain Ji Bu, China (1994).

English language translation of Wang, Z., et al., "Analysis of 9 mortal cases caused by dihydroetorphine hydrochloride abuse," *Chin. Bull. Drug Depend.* 3:176-178, Zhong Guo Yao Wu Yi Lai Xing Zo Zhi Bain Ji Bu, China (1994), 3 pages.

Wu, G., et al., "Dihydroetorphine hydrochloride for moderate and severe cancer pain," *China Cancer Journal* 13:64-67, China National Publications Import & Export Corp., Export Dept., Beijing, China (1991).

English language translation of Wu, G., et al., "Dihydroetorphine hydrochloride for moderate and severe cancer pain," *China Cancer Journal* 13:64-67, China National Publications Import & Export Corp., Export Dept., Beijing, China (1991), 8 pages.

Wu, W.-R., et al., "Immunosuppressive effects of dihydroetorphine, a potent narcotic analgesic, in dihydroetorphine-dependent mice," *European Journal of Pharmacology* 366:261-269, Elsevier Science B.V., Netherlands (1999).

Wu, W.-R., et al, "Involvement of μ-opioid receptors and α-adrenoceptors in the immunomodulatory effects of dihydroetorphine," *European Journal of Pharmacology* 353:79-85, Elsevier Science B.V., Netherlands (1998).

English language translation of Chinese package insert "Dihydroetorphine Hydrochloride Sublingual Tablets," chinapharm.com.cn, accessed at www.chinapharm.com.cn, accessed on Mar. 5, 2009, 5 pages.

Xiao, Y.-H., "Clinical observation of dihydroetorphine on cancer patients of terminal phase," *Journal of New Drugs and Clinical Remedies* 3:40-41, Shanghai Shi Yi Yao Guan Li Ju Ke Ji Qing Bao Yan Jiu Suo, Shanghai, China (1982).

English language translation of Xiao, Y.-H., "Clinical observation of dihydroetorphine on cancer patients of terminal phase," *Journal of New Drugs and Clinical Remedies* 3:40-41, Shanghai Shi Yi Yao Guan Li Ju Ke Ji Qing Bao Yan Jiu Suo, Shanghai, China (1982), 3 pages.

Yin, H., et al., "The effect of DHE on neurobehavioral teratology in offsprings of mice," *Chin. Bull. Drug Depend.* 5(3):145-150, Gai Suo, Beijing, China (1996).

English language translation of Yin, H., et al., "The effect of DHE on neurobehavioral teratology in offsprings of mice," *Chin. Bull. Drug Depend.* 5(3).145-150, Gai Suo, Beijing, China (1996), 8 pages.

Yuan, B.-L, et al., "Distribution of [$^3$H]dihydroetorphine in rat brain observed by in vitro quantitative autoradiography," *Chinese Journal of Pharmacology and Toxicology* 9:61-64, Zhongguo Yao Li Xue Hui, Beijing, China (1995).

English language translation of Wang, W., et al., "Psychological dependence potential of dihydroetorphine in Rhesus monkeys," *Chin. Bull. Drug Depend.* 6(1):8-12, Zhong Guo Yao Wu Yi Lai Xing Zo Zhi Bain Ji Bu, China (1997), 8 pages.

Yuan, S., et al., "Metabolism of [$^3$H]dihydroetorphine in mice," *Academy of Military Med Sciences* 11:46-50, Jun Shi Xue Ke Xue Yuan Yuan Kan Bian Ji Bu, China (1987).

English translation of Huang, M., et al., "Pharmacodynamics and Pharmacokinetics of Dihydroetorphine Hydrochloride Administered Sublingually in Mice and Rats," *Acta Pharmacologica Sinica* 9(4):308-312, Shanghai Ke Xue Ji Shu Chu Ban She, Shanghai, China (1988), 8 pages.

Ge, Y., et al., "Clinical assessment of physical dependence potential of dihydroetorphine hydrochloride (DHE)," *Acta. Pharm. Sinica.* 29 (4): 256-260, Shanghai Ke Xue Ji Shu Chu Ban She, Shanghai, China (1994).

Pharmacopoeia of the People's Republic of China vol. II, "New Admissions," p. XX and XXI, "Dihydroetorphine Hydrocholoride," p. 434, and "Dihydroetorphine Hydrochloride Sublingual Tablets," p. 435, Eds. He Hong mei and Cui Liping, China Medical Science Press, Beijing, China (2010), 6 pages.

Abel, A.M., et al., "Synthesis of potential buprenorphine intermediates by selective microbial N- and O-demethylation," *Biotechnology Letters* 24(15):1291-1294, Kluwer Academic Publishers, Netherlands (2002).

(56) References Cited

OTHER PUBLICATIONS

English Abstract of Japanese Patent Publication No. JP 59-184182 (FP18), date of publication Oct. 19, 1984.
Grivas, K., et al., "Acid Catalysed Rearrangements of the Thevinols: The Mechanism of Furanocodide Formation," *Tetrahedron Letters* 40:1795-1798, Elsevier Science Ltd., Netherlands (1999).
Husbands, S.M., et al., "Ring Constrained Analogues of the Orvinols: The Furanomorphides," *Bioorg.& Med. Chem. Lett. 9*: 831-834, Elsevier Science Ltd., Netherlands (1999).
Knipmeyer, L.L. and Rapoport, H., "Analgesics of the 6,14-Ethenomorphinan Type. 6-Deoxy-7α-orvinols and 6-Deoxy-8α-orvinols," *J. Med. Chem. 28*(4):461-466, American Chemical Society, United States (1985).
Sepsi, A., et al., "Investigation of the Azidolysis of Tertiary Alcohols of Thebaine Derivatives with Bridged Ring C," *Arch. Pharm. (Weinheim)* 326:313-317, VCH Verlagsgesellschaft mbH, Germany (1993).
Marton, J. et al., "Studies on the synthesis of β-thevinone derivatives," *Tetrahedron* 54:9143-9152, Elsevier Science, Great Britain (1998).
Office Action dated Feb. 4, 2014, in U.S. Appl. No. 13/133,472, Whitelock, S. et al., having a 35 U.S.C. §371(c) date of Sep. 28, 2011.
Notice of Allowance dated May 30, 2014, in U.S. Appl. No. 13/133,472, Whitelock, S. etal., having a 35 U.S.C. §371(c) date of Sep. 28, 2011.
Derrick, I., et al., "Perchloric acid induced epimerisation of the thevinones: an improved synthesis of 7β-dihydrothevinones," *Tetrahedron Letters 41*(39):7571-7576, Elsevier Science Ltd., England (2000).
Office action dated Feb. 2, 2016, in U.S. Appl. No. 14/925,406, Whitelock, S., et al., filed Oct. 28, 2015.
Notice of Allowance dated Jun. 21, 2016, in U.S. Appl. No. 14/925,406, Whitelock, S., et al., filed Oct. 28, 2015.
Office Action dated Aug. 23, 2017, in U.S. Appl. No. 15/336,970, Whitelock, S. et al., filed Oct. 28, 2016.
Office action dated May 1, 2015, in U.S. Appl. No. 14/473,751, Whitelock, S., et al., filed Aug. 29, 2014.
Notice of Allowance dated Aug. 6, 2015, in U.S. Appl. No. 14/473,751, Whitelock, S., et al., filed Aug. 29, 2014.
English language abstract of CN 1676130 (cited as document FP29 on accompanying form PTO/SB/08A), Espacenet database, Worldwide, published Oct. 5, 2005.
English language abstract of CN 1957918 (cited as document FP30 on accompanying form PTO/SB/08A), Espacenet database, Worldwide, published May 9, 2007.
Qin, Bi-Yi, "Advances in Dihydroetorphine: From Analgesia to Detoxification," *Drug Development Development Research 39*:131-134, Wiley-Liss, Inc., United States (1997).
Office Action dated Mar. 27, 2018, in U.S. Appl. No. 15/336,970, Whitelock, S. et al., filed Oct. 28, 2016.
Office Action dated Jan. 3, 2019, in U.S. Appl. No. 15/336,970, Whitelock, S. et al., filed Oct. 28, 2016.
Lötsch, J., et al., "Fatal Respiratory Depression after Multiple Intravenous Morphine Injections," *Clin. Pharmacokinet. 45*(11):1051-1060, Adis Data Information B.V., Netherlands (2006).
Racoosin, J. A., et al., "New Evidence about an Old Drug—Risk with Codeine after Adenotonsillectomy," *N. Engl. J. Med. 368*(23):2155-2157, Massachusetts Medical Society, United States (2013).
Madadi, P., et al., "Safety of codeine during breastfeeding," *Canadian Family Physician—Le Medecin de famille canadien 53*:33-35, the College of Family Physicians of Canada, Canada (2007).
Weingarten, T. N., et al., "Multimodal Analgesic Protocol and Postanesthesia Respiratory Depression During Phase I Recovery After Total Joint Arthroplasty," *Regional Anesthesia and Pain Medicine 40*(4):330-336, American Society of Regional Anesthesia and Pain Medicine (2015).
Gupta, K., et al., "Risk factors for opioid-induced respiratory depression in surgical patients: a systematic review and meta-analyses," *BMH Open 8*:e024086, pp. 1-10, BMJ, United Kingdom (2018).
Shi, J. and Zhuang, J., "Pharmacology and Clinical Application of Dihydroetorphine Hydrochloride," *Strait Pharmaceutical Journal 6*(4):37-38, China Academic Journal Electronic Publishing House, China (1994).
Unverified English language translation of Shi, J. and Zhuang, J., "Pharmacology and Clinical Application of Dihydroetorphine Hydrochloride," *Strait Pharmaceutical Journal 6*(4):37-38, China Academic Journal Electronic Publishing House, China (1994).
Office Action dated Jul. 5, 2019, in U.S. Appl. No. 15/336,970, Whitelock, S. et al., filed Oct. 28, 2016.
Reagan-Shaw, S., et al., "Dose translation from animal to human studies revisted," The FASEB Journal 22(3):659-661, Wiley Online Library, United States (2008).

\* cited by examiner

Questionnaire

1 h After Infusion Stopped

Circle ONE number only to indicate how you feel your dizziness, euphoria, nausea, sedation and your dysphoria is at the moment.

Actual Time  hh : mm circle ONE number only
0  10  20  30  40  50  60  70  80  90  100

No Dizziness — Dizziness as bad as you can imagine circle ONE number only
0  10  20  30  40  50  60  70  80  90  100

No Euphoria — Euphoria as bad as you can imagine circle ONE number only
0  10  20  30  40  50  60  70  80  90  100

No Nausea — Nausea as bad as you can imagine circle ONE number only
0  10  20  30  40  50  60  70  80  90  100

No Sedation — Sedation as bad as you can imagine circle ONE number only
0  10  20  30  40  50  60  70  80  90  100

No Dysphoria — Dysphoria as bad as you can imagine

Figure 9

DIHYDROETORPHINE FOR THE PROVISION OF PAIN RELIEF AND ANAESTHESIA

FIELD OF INVENTION

The present invention relates to a method of providing pain relief and anaesthesia in a human subject comprising administering (R)-dihydroetorphine. More specifically the invention relates to methods of providing analgesia or anaesthesia with reduced opioid-related side effects and in particular respiratory depression.

BACKGROUND

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, Pain, in Cecil Textbook of Medicine 100-107 (J. C. Bennett and F. Plum eds., 20th ed. 1996)). Pain can also be classified into different acute, subacute and chronic types including nociceptive, inflammatory, neuropathic or mixed pain. This includes visceral, somatic, radicular, neuralgic, central pain, pain associated with amputation, complex regional pain syndromes and fibromylagia.

Pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone.

Opioid analgesics form the cornerstone of contemporary treatment of moderate to severe (acute and chronic) pain. Pain relief occurs in different clinical settings. Pain treatment is critical in the management and treatment of many diseases wherein pain is experienced as a symptom and/or as a side effect. Pain treatment is also critical during anaesthesia. Opioids, however, come with a series of side effects of which opioid-induced respiratory depression (OIRD) is potentially life threatening. In recent years the number of lethal opioid-related respiratory complications has increased significantly, mainly due to the increase in opioid use, misuse or abuse of legally prescribed opioids for moderate to severe non-chronic cancer pain (most importantly lower back pain). Opioids produce respiratory depression via activation of the µ-opioid receptors (MORs) expressed on pontine neurons involved in the ventilatory control.

A wide range of opioid analgesics are known. Opioid agonists include, for example, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papavereturn, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures of any two or more of the foregoing.

Another known opioid analgesic is (R)-dihydroetorphine (R-DHE) shown below.

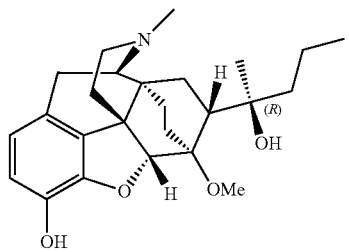

Compared to other opioid analgesics its properties have been investigated to a far lesser extent. Clinically it has only been used in humans in China in injectable and more recently sublingual form.

Fentanyl is currently the most commonly used opioid analgesic for the treatment of moderate to severe pain in clinical settings. It is usually administered intravenously (as a bolus or infusion). Low doses, e.g. 50-200 µg and low infusion rates, e.g. 0.05-0.08 µg/kg/minutes are necessary if spontaneous ventilation is to be maintained because fentanyl produces a dose dependent respiratory depression with apnoea at high dose.

Fentanyl, and other members of the fentanyl family, is also the most commonly used opioid analgesic in anaesthesia. Following intravenous administration in a non-premedicated adult patient, fentanyl is expected to provide adequate analgesia for 10-20 minutes in surgical procedures involving low pain intensity. A bolus of fentanyl is expected to provide analgesia for about one hour and the analgesia produced is generally adequate for surgery involving moderate pain intensity. Administration of 50 microgram/kg will provide intense analgesia for some four to six hours for surgery associated with intense stimulation. Ventilated patients may be given a loading dose as a fast infusion of approximately 1 microgram/kg/minute for the first 10 minutes, followed by an infusion of approximately 0.1 microgram/kg/minute. Alternatively, the loading dose may be administered as a bolus. Due to the dose dependent respiratory depression associated with fentanyl, patients receiving fentanyl require careful and close monitoring during administration of the drug and for a prolonged period thereafter. The SPC for fentanyl also confirms that it should only be given in an environment where the airway can be controlled, resuscitation equipment is available and opioid antagonists are readily available.

Fentanyl additionally causes a number of other undesirable effects including, for example, nausea, vomiting, dizziness, mental clouding, dysphoria, pruritus, constipation, increased biliary tract pressure, urinary retention and hypotension. The development of tolerance to fentanyl and the risk of dependence and abuse for fentanyl is another undesirable effect.

As a result there is a continuing need for analgesic medications able to provide high efficacy pain relief while reducing the extent of undesired side effects.

SUMMARY OF INVENTION

Viewed from a first aspect the present invention provides a method of providing pain relief in a human subject in need thereof comprising administering (R)-dihydroetorphine to said subject, wherein said (R)-dihydroetorphine is administered in a dose of at least 0.01 µg/kg, more preferably at least 0.05 µg/kg, and the level of respiratory depression in said subject is 65 or less % relative to the baseline level pre-administration of (R)-dihydroetorphine and/or the level of respiration (e.g. as characterised by respiration minute volume and measured as described herein) is 35 to 100% relative to the baseline level pre-administration of (R)-dihydroetorphine.

Viewed from a further aspect the present invention provides a method of providing pain relief in a human subject in need thereof comprising administering (R)-dihydroetorphine to said subject, wherein said (R)-dihydroetorphine is administered in a dose of at least 0.01 µg/kg, preferably at least 0.05 µg/kg, and the peak respiratory depression in said subject is 20 to 80% relative to the baseline level pre-administration of (R)-dihydroetorphine.

Viewed from a further aspect the present invention provides a method of providing analgesia in a human subject in need thereof comprising administering (R)-dihydroetorphine to said subject, wherein said (R)-dihydroetorphine is administered in a dose of at least 0.01 µg/kg, preferably at least 0.05 µg/kg, and the ventilation ratio in said subject is at least 0.3.

Viewed from a further aspect the present invention provides a method of providing pain relief in a human subject in need thereof comprising administering (R)-dihydroetorphine to said subject, wherein said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides a method of providing pain relief in a human subject in need thereof comprising administering (R)-dihydroetorphine to said subject, wherein said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides a method of providing pain relief in a human subject in need thereof comprising administering (R)-dihydroetorphine to said subject, wherein said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides a method of providing pain relief to a human subject in need thereof comprising administering (R)-dihydroetorphine to said subject, wherein said (R)-dihydroetorphine is administered in a dose that increases the pain threshold value relative to the baseline level pre-administration of (R)-dihydroetorphine by at least 1.2 times and the level of respiratory depression in said subject is 65% or less relative to the baseline level pre-administration of (R)-dihydroetorphine.

Viewed from a further aspect the present invention provides a method of providing pain relief in a human subject in need thereof whilst minimising risk of apnoea comprising administering a dose of (R)-dihydroetorphine that provides dose dependent pain relief and dose-independent respiratory depression.

Viewed from a further aspect the present invention provides a method of providing maximum pain relief in a human subject in need thereof whilst minimising risk of apnoea comprising administering a dose of (R)-dihydroetorphine which causes a $E_{MIN}$ in ventilation of 30-50% relative to the baseline level pre-administration of (R)-dihydroetorphine.

Viewed from a further aspect the present invention provides a method of treating pain in a human subject comprising administering to said subject an effective dose of (R)-dihydroetorphine, wherein during said treating at least one opioid-related side effect is reduced compared to treatment with an equianalgesic dose of fentanyl.

Viewed from a further aspect the present invention provides a method of treating pain in a human subject comprising administering to said subject an effective dose of (R)-dihydroetorphine, wherein during said treating opioid-related respiratory depression is 65% or less relative to the baseline level pre-administration of (R)-dihydroetorphine and at least one of the following criteria defining the levels of opioid-related side effects is satisfied in the 7.5 hours post administration of (R)-dihydroetorphine:
average NAS score for dizziness of less than 50
average NAS score for euphoria of less than 60
average NAS score for nausea of less than 40
average NAS score for sedation of less than 60
average NAS score for dysphoria of less than 40.

Viewed from a further aspect the present invention provides a method of providing anaesthesia in a human subject in need thereof comprising administering (R)-dihydroetorphine to said subject, wherein said (R)-dihydroetorphine is administered in a dose of at least 0.15 µg/kg and the level of respiratory depression in said subject is 65 or less % relative to the baseline level pre-administration of (R)-dihydroetorphine and/or the level of respiration (e.g. as characterised by respiration minute volume and measured as described herein) is 35 to 100% relative to the baseline level pre-administration of (R)-dihydroetorphine.

Viewed from a further aspect the present invention provides a method of providing anaesthesia in a human subject in need thereof comprising administering (R)-dihydroetorphine to said subject, wherein said (R)-dihydroetorphine is administered in a dose of at least 0.15 µg/kg and the peak respiratory depression in said subject is 20 to 80% relative to the baseline level pre-administration of (R)-dihydroetorphine.

Viewed from a further aspect the present invention provides a method of providing anaesthesia in a human subject in need thereof comprising administering (R)-dihydroetorphine to said subject, wherein said (R)-dihydroetorphine is administered in a dose of at least 0.15 µg/kg and the resulting ventilation ratio in said subject is at least 0.3.

Viewed from a further aspect the present invention provides a method of providing anaesthesia in a human subject in need thereof comprising administering (R)-dihydroetorphine to said subject, wherein said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides a method of providing anaesthesia in a human subject in need thereof comprising administering (R)-dihydroetorphine to said subject, wherein said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides a method of providing anaesthesia in a human subject in need thereof comprising administering (R)-dihydroetorphine to said subject, wherein said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides a method of providing anaesthesia to a human subject in need thereof comprising administering (R)-dihydroetorphine to said subject, wherein said (R)-dihydroetorphine is administered in a dose that increases the pain threshold value relative to the baseline level pre-administration of (R)-dihydroetorphine by at least 1.5 times and the level of respiratory depression in said subject is 65% or less relative to the baseline level pre-administration of (R)-dihydroetorphine.

Viewed from a further aspect the present invention provides a method of providing anaesthesia in a human subject in need thereof whilst minimising risk of apnoea comprising administering a dose of (R)-dihydroetorphine that provides dose dependent pain relief and dose-independent respiratory depression.

Viewed from a further aspect the present invention provides a method of providing maximum anaesthesia in a human subject in need thereof whilst minimising risk of apnoea comprising administering a dose of (R)-dihydroetorphine which causes a $E_{MIN}$ in ventilation of 30-50% relative to the baseline level pre-administration of (R)-dihydroetorphine.

Viewed from a further aspect the present invention provides a method of providing anaesthesia in a human subject comprising administering to said subject an effective dose of (R)-dihydroetorphine, wherein during said treating at least one opioid-related side effect is reduced compared to treatment with an equianalgesic dose of fentanyl.

Viewed from a further aspect the present invention provides a method of providing anaesthesia in a human subject comprising administering to said subject an effective dose of (R)-dihydroetorphine, wherein during said treating opioid-related respiratory depression is 65% or less relative to the baseline level pre-administration of (R)-dihydroetorphine and at least one of the following criteria defining the levels of opioid-related side effects is satisfied in the 7.5 hours post administration of (R)-dihydroetorphine:
average NAS score for dizziness of 0 to 50
average NAS score for euphoria of 0 to 60
average NAS score for nausea of 0 to 40
average NAS score for sedation of 0 to 60
average NAS score for dysphoria of 0 to 40.

Viewed from a further aspect the present invention provides a method of providing pain relief or anaesthesia in a human subject in need thereof comprising administering (R)-dihydroetorphine to said subject, wherein said (R)-dihydroetorphine is administered in a dose of 0.20 to 0.5 µg/kg and the level of respiratory depression in said subject is 85 or less % relative to the baseline level pre-administration of (R)-dihydroetorphine and/or the level of respiration (e.g. as characterised by respiration minute volume and measured as described herein) is 15 to 100% relative to the baseline level pre-administration of (R)-dihydroetorphine.

Viewed from a further aspect the present invention provides a method of providing pain relief or anaesthesia in a human subject in need thereof comprising administering (R)-dihydroetorphine to said subject, wherein said (R)-dihydroetorphine is administered in a dose of 0.20 to 0.5 µg/kg and the peak respiratory depression in said subject is 15 to 80% relative to the baseline level pre-administration of (R)-dihydroetorphine.

Viewed from a further aspect the present invention provides a method of providing pain relief or anaesthesia in a human subject in need thereof comprising administering (R)-dihydroetorphine to said subject, wherein said (R)-dihydroetorphine is administered in a dose of 0.20 to 0.5 µg/kg and the resulting ventilation ratio in said subject is at least 0.15. Viewed from a further aspect the present invention provides (R)-dihydroetorphine for the treatment of pain, wherein during said treatment said (R)-dihydroetorphine is administered in a dose of at least 0.01 µg/kg, preferably at least 0.05 µg/kg, and the level of respiratory depression in said subject is 65% or less relative to the baseline level pre-administration of (R)-dihydroetorphine.

Viewed from a further aspect the present invention provides (R)-dihydroetorphine for the treatment of pain, wherein during said treatment said (R)-dihydroetorphine is administered in a dose of at least 0.01 µg/kg, preferably at least 0.05 µg/kg, and the peak respiratory depression in said subject is 20 to 80% or less relative to the baseline level pre-administration of (R)-dihydroetorphine.

Viewed from a further aspect the present invention provides (R)-dihydroetorphine for the treatment of pain, wherein during said treatment said (R)-dihydroetorphine is administered in a dose of at least 0.01 µg/kg, preferably at least 0.05 µg/kg, and the ventilation ratio in said subject is at least 0.3.

Viewed from a further aspect the present invention provides (R)-dihydroetorphine for the treatment of pain, wherein during said treatment said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides (R)-dihydroetorphine for the treatment of pain, wherein during said treatment said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides (R)-dihydroetorphine for the treatment of pain, wherein during said treatment said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides (R)-dihydroetorphine for the treatment of pain, wherein during said treatment said (R)-dihydroetorphine is administered in a dose that increases the pain threshold value relative to the baseline level pre-administration of (R)-dihydroetorphine by at least 1.2 times and the level of respiratory depression in said subject is 65% or less relative to the baseline level pre-administration of (R)-dihydroetorphine.

Viewed from a further aspect the present invention provides (R)-dihydroetorphine for the treatment of pain whilst minimising risk of apnoea, wherein during said treatment a dose of (R)-dihydroetorphine that provides dose dependent pain relief and dose-independent respiratory depression is administered.

Viewed from a further aspect the present invention provides (R)-dihydroetorphine for the treatment of pain whilst minimising risk of apnoea, wherein during said treatment a dose of (R)-dihydroetorphine which causes a $E_{MIN}$ in ventilation of 30-50% relative to the baseline level pre-administration of (R)-dihydroetorphine is administered.

Viewed from a further aspect the present invention provides (R)-dihydroetorphine for the treatment of pain, wherein during said treatment at least one opioid-related side effect is reduced compared to treatment with an equianalgesic dose of fentanyl.

Viewed from a further aspect the present invention provides (R)-dihydroetorphine for the treatment of pain, wherein during said treatment opioid-related respiratory depression is 65% or less relative to the baseline level pre-administration of (R)-dihydroetorphine and at least one of the following criteria is satisfied in the 7.5 hours post administration of (R)-dihydroetorphine:
average NAS score for dizziness of less than 50
average NAS score for euphoria of less than 60
average NAS score for nausea of less than 40
average NAS score for sedation of less than 60
average NAS score for dysphoria of less than 40.

Viewed from a further aspect the present invention provides (R)-dihydroetorphine for providing anaesthesia, wherein during said treatment said (R)-dihydroetorphine is administered in a dose of at least 0.15 μg/kg and the level of respiratory depression in said subject is 65% or less relative to the baseline level pre-administration of (R)-dihydroetorphine.

Viewed from a further aspect the present invention provides (R)-dihydroetorphine for providing anaesthesia, wherein during said treatment said (R)-dihydroetorphine is administered in a dose of at least 0.15 μg/kg and the peak respiratory depression in said subject is 20 to 80% or less relative to the baseline level pre-administration of (R)-dihydroetorphine.

Viewed from a further aspect the present invention provides (R)-dihydroetorphine for providing anaesthesia, wherein during said treatment said (R)-dihydroetorphine is administered in a dose of at least 0.15 μg/kg and the ventilation ratio in said subject is at least 0.3.

Viewed from a further aspect the present invention provides (R)-dihydroetorphine for providing anaesthesia, wherein during said treatment said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides (R)-dihydroetorphine for providing anaesthesia, wherein during said treatment said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides (R)-dihydroetorphine for providing anaesthesia, wherein during said treatment said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides (R)-dihydroetorphine for providing anaesthesia, wherein during said treatment said (R)-dihydroetorphine is administered in a dose that increases the pain threshold value relative to the baseline level pre-administration of (R)-dihydroetorphine by at least 1.5 times and the level of respiratory depression in said subject is 65% or less relative to the baseline level pre-administration of (R)-dihydroetorphine.

Viewed from a further aspect the present invention provides (R)-dihydroetorphine for providing anaesthesia whilst minimising risk of apnoea, wherein during said treatment a dose of (R)-dihydroetorphine that provides dose dependent pain relief and dose-independent respiratory depression is administered.

Viewed from a further aspect the present invention provides (R)-dihydroetorphine for providing anaesthesia whilst minimising risk of apnoea, wherein during said treatment a dose of (R)-dihydroetorphine which causes a $E_{MIN}$ in ventilation of 30-50% relative to the baseline level pre-administration of (R)-dihydroetorphine is administered.

Viewed from a further aspect the present invention provides (R)-dihydroetorphine for providing anaesthesia, wherein during said treatment at least one opioid-related side effect is reduced compared to treatment with an equianalgesic dose of fentanyl.

Viewed from a further aspect the present invention provides (R)-dihydroetorphine for providing anaesthesia, wherein during said treatment opioid-related respiratory depression is 65% or less relative to the baseline level pre-administration of (R)-dihydroetorphine and at least one of the following criteria is satisfied in the 7.5 hours post administration of (R)-dihydroetorphine:
average NAS score for dizziness of 0 to 50
average NAS score for euphoria of 0 to 60
average NAS score for nausea of 0 to 40
average NAS score for sedation of 0 to 60
average NAS score for dysphoria of 0 to 40.

Viewed from a further aspect the present invention provides (R)-dihydroetorphine for providing pain relief or anaesthesia, wherein said (R)-dihydroetorphine is administered in a dose of 0.20 to 0.5 μg/kg and the level of respiratory depression in the subject is 85% or less relative to the baseline level pre-administration of (R)-dihydroetorphine.

Viewed from a further aspect the present invention provides (R)-dihydroetorphine for providing pain relief or anaesthesia, wherein said (R)-dihydroetorphine is administered in a dose of 0.20 to 0.5 μg/kg and the peak respiratory depression in the subject is 15 to 80% or less relative to the baseline level pre-administration of (R)-dihydroetorphine.

Viewed from a further aspect the present invention provides (R)-dihydroetorphine for providing pain relief or anaesthesia, wherein said (R)-dihydroetorphine is administered in a dose of 020 to 0.5 μg/kg and the ventilation ratio in the subject is at least 0.15.

Viewed from a further aspect the present invention provides use of (R)-dihydroetorphine in the manufacture of a medicament for the treatment of pain, wherein during said treatment said (R)-dihydroetorphine is administered in a dose of at least 0.01 μg/kg, preferably at least 0.05 μg/kg, and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for the treatment of pain, wherein during treatment said (R)-dihydroetorphine is administered in a dose of at least 0.01 μg/kg, preferably at least 0.05 μg/kg, and the peak respiratory depression in said subject is 20 to 80% relative to the baseline level pre-administration of (R)-dihydroetorphine.

Viewed from a further aspect the present invention provides use of (R)-dihydroetorphine in the manufacture of a medicament for the treatment of pain, wherein during said treatment said (R)-dihydroetorphine is administered in a dose of at least 0.01 µg/kg, preferably at least 0.05 µg/kg and the ventilation ratio in said subject is at least 0.3.

Viewed from a further aspect the present invention provides use of (R)-dihydroetorphine in the manufacture of a medicament for the treatment of pain, wherein during said treatment said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for the treatment of pain, wherein during said treatment said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides use of (R)-dihydroetorphine in the manufacture of a medicament for the treatment of pain, wherein during said treatment said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for the treatment of pain, wherein during said treatment said (R)-dihydroetorphine is administered in a dose that increases the pain threshold value relative to the baseline level pre-administration of (R)-dihydroetorphine by at least 1.2 times and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for the treatment of pain, wherein during said treatment a dose of (R)-dihydroetorphine that provides dose dependent pain relief and dose-independent respiratory depression is administered.

Viewed from a further aspect the present invention provides use of (R)-dihydroetorphine in the manufacture of a medicament for the treatment of pain, wherein during said treatment a dose of (R)-dihydroetorphine which causes a $E_{MIN}$ in ventilation of 30-50% relative to the baseline level pre-administration of (R)-dihydroetorphine is administered.

Viewed from a further aspect the present invention provides use of (R)-dihydroetorphine in the manufacture of a medicament for the treatment of pain, wherein during said treatment at least one opioid-related side effect is reduced compared to treatment with an equianalgesic dose of fentanyl.

Viewed from a further aspect the present invention provides use of (R)-dihydroetorphine in the manufacture of a medicament for the treatment of pain, wherein during said treatment opioid-related respiratory depression is 65% or less relative to the baseline level pre-administration of (R)-dihydroetorphine and at least one of the following criteria is satisfied in the 7.5 hours post administration of (R)-dihydroetorphine:
average NAS score for dizziness of less than 50
average NAS score for euphoria of less than 60
average NAS score for nausea of less than 40
average NAS score for sedation of less than 60
average NAS score for dysphoria of less than 40.

Viewed from a further aspect the present invention provides use of (R)-dihydroetorphine in the manufacture of a medicament for providing anaesthesia, wherein during said treatment said (R)-dihydroetorphine is administered in a dose of at least 0.15 µg/kg and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for providing anaesthesia, wherein during treatment said (R)-dihydroetorphine is administered in a dose of at least 0.15 µg/kg and the peak respiratory depression in said subject is 20 to 80% relative to the baseline level pre-administration of (R)-dihydroetorphine.

Viewed from a further aspect the present invention provides use of (R)-dihydroetorphine in the manufacture of a medicament for providing anaesthesia, wherein during said treatment said (R)-dihydroetorphine is administered in a dose of at least 0.15 µg/kg and the ventilation ratio in said subject is at least 0.3.

Viewed from a further aspect the present invention provides use of (R)-dihydroetorphine in the manufacture of a medicament for providing anaesthesia, wherein during said treatment said (R)-dihydroetorphine is administered in a dose greater than the $ED_{75}$ dose and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for providing anaesthesia, wherein during said treatment said (R)-dihydroetorphine is administered in a dose greater than the $ED_{50}$ dose and less than the $ED_{75}$ dose and the level of respiratory depression in said subject is 50% or less relative to the baseline level pre-administration of (R)-dihydroetorphine.

Viewed from a further aspect the present invention provides use of (R)-dihydroetorphine in the manufacture of a medicament for providing anaesthesia, wherein during said treatment said (R)-dihydroetorphine is administered in a dose greater than the $ED_{75}$ dose and less than the $ED_{95}$ dose and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for providing anaesthesia, wherein during said treatment said (R)-dihydroetorphine is administered in a dose that increases the pain threshold value relative to the baseline level pre-administration of (R)-dihydroetorphine by at least 1.5 times and the level of respiratory depression in said subject is 65% or less relative to the baseline level pre-administration of (R)-dihydroetorphine.

Viewed from a further aspect the present invention provides use of (R)-dihydroetorphine in the manufacture of a medicament for providing anaesthesia, wherein during said treatment a dose of (R)-dihydroetorphine that provides dose dependent pain relief and dose-independent respiratory depression is administered.

Viewed from a further aspect the present invention provides use of (R)-dihydroetorphine in the manufacture of a medicament for providing anaesthesia, wherein during said treatment a dose of (R)-dihydroetorphine which causes a $E_{MIN}$ in ventilation of 30-50% relative to the baseline level pre-administration of (R)-dihydroetorphine is administered.

Viewed from a further aspect the present invention provides use of (R)-dihydroetorphine in the manufacture of a medicament for providing anaesthesia, wherein during said treatment at least one opioid-related side effect is reduced compared to treatment with an equianalgesic dose of fentanyl.

Viewed from a further aspect the present invention provides use of (R)-dihydroetorphine in the manufacture of a medicament for providing anaesthesia, wherein during said treatment opioid-related respiratory depression is 65% or less relative to the baseline level pre-administration of (R)-dihydroetorphine and at least one of the following criteria is satisfied in the 7.5 hours post administration of (R)-dihydroetorphine:

average NAS score for dizziness of 0 to 50
average NAS score for euphoria of 0 to 60
average NAS score for nausea of 0 to 40
average NAS score for sedation of 0 to 60
average NAS score for dysphoria of 0 to 40.

Viewed from a further aspect the present invention provides use of (R)-dihydroetorphine in the manufacture of a medicament for the treatment of pain or anaesthesia, wherein during said treatment said (R)-dihydroetorphine is administered in a dose of 0.20 to 0.5 µg/kg and the level of respiratory depression in said subject is 85% or less relative to the baseline level pre-administration of (R)-dihydroetorphine.

Viewed from a further aspect the present invention provides use of (R)-dihydroetorphine in the manufacture of a medicament for the treatment of pain or anaesthesia, wherein during said treatment said (R)-dihydroetorphine is administered in a dose of 0.20 to 0.5 µg/kg and the peak respiratory depression in said subject is 15 to 80% relative to the baseline level pre-administration of (R)-dihydroetorphine.

Viewed from a further aspect the present invention provides use of (R)-dihydroetorphine in the manufacture of a medicament for the treatment of pain or anaesthesia, wherein during said treatment said (R)-dihydroetorphine is administered in a dose of 0.20 to 0.5 µg/kg and the ventilation ratio in said subject is at least 0.3.

Definitions

As used herein the term "pain" refers to an unpleasant feeling that is conveyed to the brain by sensory neurons called nociceptors.

As used herein the term "nociceptive pain" refers to pain caused by tissue injury detected by nociceptors at the site of injury. After the injury, the site becomes a source of ongoing pain and tenderness.

As used herein the terms "pain relief" and "analgesia" refer to the removal and/or reduction in pain resulting from the action of a drug. The terms are used herein synonymously.

As used herein the term "anaesthesia" means a loss of consciousness, sensation, or awareness resulting from pharmacological depression of nerve function.

As used herein the term "sedation" refers to the calming of mental excitement or abatement of physiological function by administration of a drug called a sedative.

As used herein, the term "effective amount" means the amount of drug needed to reach an analgesic effect.

As used herein the term "opioid" refers to natural, semi-synthetic and synthetic drugs that have opioid-like effects similar to morphine.

As used herein the term "side effect" refers to an effect of a drug, e.g. opioid, that is not the intended therapeutic effect. The term "opioid-related side effect" refers to non-therapeutic effects caused by opioids. Respiratory depression is an example of an opioid-related side effect.

As used herein the terms "respiration" and "ventilation" are used to refer to the flow of air into the lungs. Generally the terms are used herein interchangeably. Respiration may be characterised by respiration minute volume (or minute ventilation) which is the volume of gas inhaled or exhaled from the lungs per minute. Unless otherwise specified the term respiration refers to average respiration.

As used herein the term "respiratory depression" refers to a decrease in the respiration minute volume. Respiratory depression may manifest as shortness of breath and/or a slowing in rate of breathing. A respiratory depression of 100% indicates apnoea. A respiratory depression of 40% indicates that the respiration minute volume is 60% of the baseline value. Respiratory depression may be measured by different techniques as described below. Unless specified otherwise, the term respiratory depression refers to average respiratory depression. As used herein the term "peak respiratory depression" refers to the maximum level of respiratory depression that is detected during measurement of respiration over a period of time, e.g. 1 hour.

As used herein the term "ventilation ratio" refers to the ratio of the average level of respiration or ventilation post-administration of drug to the average level of respiration or ventilation pre-administration of drug, e.g. as determined according to the method set out in the examples herein. A value of less than 1 therefore indicates a decrease in ventilation, i.e. respiratory depression.

As used herein the term "dizziness" refers to a sensation of unsteadiness, often accompanied by a feeling of movement within the head.

As used herein the term "euphoria" refers to a feeling of elation or well being.

As used herein the term "nausea" refers to the sensation of being about to vomit.

As used herein the term "sedation" refers to a decrease in attention, mental awareness, focus, and state of consciousness and manifests in a lack of physical strength (muscle fatigue), lack of voluntary activity, lethargy, drowsiness, and sleep.

As used here the term "dysphoria" refers to an emotional state characterised by anxiety, depression and restlessness.

As used herein the term "apnoea" refers to the cessation of rhythmic breathing for 60 seconds or more.

As used herein the term "equianalgesic" refers to a dose of drug that provides substantially the same level of analgesia as a given amount of another drug. The amounts of each drug may be different, but the level of analgesia provided is the same.

As used herein the term "ceiling effect" refers to the achievement of a maximum effect regardless of an increase in drug dose. In other words the effect plateaus. This means that increasing the drug dose further will not increase the effect that has a ceiling any further.

As used herein the term "dose-independent respiratory depression" refers to the occurrence of a ceiling effect or plateauing in respiratory depression that does not cause apnoea. This means that further increases in the drug dose will not increase the respiratory depression any further.

As used herein the term "$E_{MIN}$" refers to the asymptotic minimum in respiration or ventilation.

As used herein the term "$ED_{50}$" refers to the dose causing a 50% reduction in respiration or ventilation relative to the baseline value pre-administration of the drug. Analogously the terms "$ED_{75}$", "$ED_{85}$" and "$ED_{90}$" refers to the dose causing a 75%, 85% and 90% reduction in ventilation relative to the baseline value pre-administration of the drug respectively.

As used herein the NAS score is on a scale of 0 to 100 where 0 is no effect and 100 is worst imaginable effect.

DETAILED DESCRIPTION OF THE INVENTION

The present invention generally relates to methods of treating pain or providing analgesia. The methods of the invention may alleviate pain or may reduce the level of pain. Preferably the methods of the invention alleviate or remove pain. The methods of the present invention include treating pain or providing analgesia during anaesthesia.

In the methods of the invention, pain relief or analgesia, whether during anaesthesia or not, is treated by administering (R)-dihydroetorphine, which is an opioid, whilst controlling respiratory depression and minimising other side effects conventionally associated with opioid treatment. The common occurrence of side effects during opioid treatment is disadvantageous for several reasons. In some cases side effects, e.g. respiratory depression, can endanger a subject's life and in extreme cases lead to fatality. More commonly side effects (e.g. nausea, dysphoria) negatively impact either physically and/or psychologically on subjects and in almost all cases side effects reduce patient compliance to a treatment regime.

It has been surprisingly found that the level of respiratory depression associated with methods of treating pain by administering (R)-dihydroetorphine exhibits a ceiling effect. In other words the level of respiratory depression associated with administration of (R)-dihydroetorphine reaches a maximum and further increases in the dose of (R)-dihydroetorphine administered do not impact on the level of respiratory depression observed. Even more significantly the ceiling effect is achieved in the analgesic window. This means that the treatment of pain by administration of (R)-dihydroetorphine, e.g. in certain doses, is significantly safer and less likely to result in opioid-induced respiratory depression, than treatment with other opioids such as fentanyl. This is particularly advantageous when the treatment of pain is during anaesthesia wherein the highest doses of (R)-dihydroetorphine tend to be used.

The level of respiratory depression associated with an opioid, e.g. (R)-dihydroetorphine, treatment may be quantified versus the baseline respiration level, i.e. the respiration level pre administration of the drug. Preferably the average level of respiratory depression is determined by measuring the average level of respiration pre and post administration of the opioid, e.g. as described in the examples. A respiratory depression of 0% means that the levels of respiration pre and post administration of the opioid are identical. A respiratory depression of 100% means that post administration of the opioid apnoea occurs. A respiratory depression of 30% means that post administration of the drug the level of respiration is reduced by 30% and the level of respiration is 70% of the pre administration level. Respiratory depression is therefore the level of reduction in respiration relative to the pre administration level. Preferably the pre administration average respiratory function is measured for 1 hour prior to administration of the drug.

In the methods of the present invention the average and peak respiratory depression is preferably measured under iso-hypercapnic conditions for, e.g. 1 hour following administration of said (R)-dihydroetorphine. Preferably the (R)-dihydroetorphine is administered intravenously. Preferably the dose of (R)-dihydroetorphine is administered over 10 minutes. The 1 hour over which measurement is made commences following the administration of (R)-dihydroetorphine.

The measurement of average respiratory depression is preferably carried out by the end-tidal forcing technique wherein end-tidal $PCO_2$ and end tidal $PO_2$ are forced to follow a specific pattern over time. Advantageously this ensures that the ventilatory response of the test opioid is independent of effects of confounding changes in arterial $CO_2$ and independent of the speed of administration of the drug. Preferably the level of respiratory depression is measured as described in the examples herein. Particularly preferably the average respiratory depression is measured under iso-hypercapnic conditions for 10 to 120 minutes, more preferably 30 to 90 minutes and still more preferably 1 hour post-administration of (R)-dihydroetorphine with end tidal oxygen level clamped at 110 mmHg and end tidal carbon dioxide clamped at a level causing ventilation levels of 20±2 L/min. Preferably the end tidal carbon dioxide level is clamped at 50 mmHg. Preferably the level of respiration or ventilation is measured continuously.

In some preferred methods of the invention, the average respiratory depression, e.g. as measured under the above conditions, is 0 to 65%, more preferably 0 to 60%, still more preferably 0 to 50%, yet more preferably 0 to 45% and even more preferably 0 to 35% relative to the baseline level prior to administration of the (R)-dihydroetorphine. In further preferred methods of the invention, the average respiratory depression e.g. as measured under the above conditions, is 20 to 65%, more preferably 40 to 65% and still more preferably 50 to 65% relative to the baseline level prior to administration of (R)-dihydroetorphine. A smaller % of respiratory depression is advantageous, with a value of 0% indicating that no respiratory depression occurs as a result of administration of the drug.

Thus in preferred methods of the invention the level of respiration, e.g. as characterised by respiration minute volume and measured as described above, is 35 to 100%, more preferably 40 to 100%, still more preferably 50 to 100%, yet more preferably 55 to 100% and even more preferably 65 to 100% relative to the baseline respiration level prior to administration of the (R)-dihydroetorphine. In further preferred methods of the invention, the average respiration, e.g. as characterised by respiration minute volume and measured as described above, is 35 to 80%, more preferably 35 to 60% and still more preferably 35 to 50% relative to the baseline respiration level prior to administration of the (R)-dihydroetorphine.

The peak respiratory depression may also be measured by the above-described technique. The measurement of peak respiratory depression is preferably carried out by the end-tidal forcing technique wherein end-tidal $PCO_2$ and end tidal $PO_2$ are forced to follow a specific pattern over time. The peak respiratory depression is the highest level of respiratory depression measured under iso-hypercapnic conditions for 10 to 120 minutes, more preferably 30 to 90 minutes and still more preferably 1 hour post-administration of (R)-dihydroetorphine with end tidal oxygen level clamped at 110 mmHg and end tidal carbon dioxide clamped at a level causing ventilation levels of 20±2 L/min as described above. Preferably the end tidal carbon dioxide level is clamped at 50 mmHg. When measuring peak respiratory depression, the level of respiration or ventilation is preferably measured continuously.

In some preferred methods of the invention, the peak respiratory depression is 20 to 80%, more preferably 45 to 75%, still more preferably 50 to 70% and yet more preferably 60 to 70% relative to the baseline level prior to administration of (R)-dihydroetorphine. In further preferred methods of the invention, the nadir in respiration level is 20 to 80%, more preferably 25 to 55%, still more preferably 30 to 50% and yet more preferably 30 to 40% relative to the baseline level prior to administration of (R)-dihydroetorphine.

Respiratory depression may alternatively be quantitated in terms of a ventilation ratio. The ventilation ratio is the ratio of average respiration in the 1 hour post administration of (R)-dihydroetorphine to the average respiration pre-administration of (R)-dihydroetorphine. The pre administration respiration is measured for 1 hour prior to administration of the drug. Thus a high ventilation ratio corresponds to a low level of respiratory depression. In preferred methods of the present invention the ventilation ratio in the subject is at least 0.3. More preferably the ventilation ratio in the subject is between 0.3 and 0.6, still more preferably 0.35 to 0.55 and yet more preferably 0.4 to 0.45.

Preferably the ventilation ratio is determined by measuring respiration pre-administration of (R)-dihydroetorphine for 1 hour and for 1 hour post-administration of (R)-dihydroetorphine under iso-hypercapnic conditions. Particularly preferably the ventilation ratio is determined by measuring respiration pre-administration of (R)-dihydroetorphine and for 10 to 120 minutes, more preferably 30 to 90 minutes and still more preferably 1 hour post-administration administration of (R)-dihydroetorphine under iso-hypercapnic conditions with end tidal oxygen level clamped at 110 mmHg and end tidal carbon dioxide clamped at a level causing ventilation levels of 20±2 L/min. Yet more preferably the end tidal carbon dioxide level is clamped at 50 mmHg. Preferably respiration or ventilation is measured continuously.

The above-described methods for measuring peak and average respiratory depression are under forced conditions. Average respiratory depression may be alternatively measured in a physiological setting by measuring oxygen saturation levels ($SpO_2$) prior to and post administration of (R)-dihydroetorphine. $SpO_2$ levels may be determined using an oximeter according to conventional procedures.

The pre administration level of $SpO_2$ is preferably measured for 1 hour prior to administration of the drug. The post administration $SpO_2$ is preferably measured for 1 hour following administration of the (R)-dihydroetorphine. The average respiratory depression is the ratio of the average $SpO_2$ level post administration to the average $SpO_2$ level pre administration×100. Preferably the (R)-dihydroetorphine is administered intravenously. Preferably the dose of (R)-dihydroetorphine is administered over 10 minutes. The 1 hour over which measurement is made commences following the administration of (R)-dihydroetorphine.

When determined in a clinical setting using $SpO_2$ levels, the average respiratory depression is 0 to 10%, more preferably 0 to 7.5%, still more preferably 0 to 5%, yet more preferably 0 to 2.5% and even more preferably 0 to 2% relative to the baseline level prior to administration of the (R)-dihydroetorphine. In such preferred methods the average respiration, e.g. as characterised by respiration minute volume and measured using $SpO_2$ levels, is 90 to 100%, more preferably 92.5 to 100%, still more preferably 95 to 100% and yet more preferably 98 to 100% relative to the baseline respiration level prior to administration of the (R)-dihydroetorphine.

In preferred methods of the invention, e.g. for providing pain relief or analgesia, (R)-dihydroetorphine is administered in a dose of 0.01 to 1 µg/kg, more preferably 0.02 to 0.75 µg/kg, still more preferably 0.03 to 0.5 µg/kg and yet more preferably 0.03 to 0.4 µg/kg. Particularly preferably the (R)-dihydroetorphine is administered in a dose of 0.04 to 0.25 µg/kg, more preferably 0.05 to 0.175 µg/kg, still more preferably 0.06 to 0.16 µg/kg and yet more preferably 0.075 to 0.15 µg/kg. Still more preferably the dose of (R)-dihydroetorphine is 0.075 µg/kg, 0.125 µg/kg, 0.15 µg/kg, 0.20 µg/kg or 0.25 µg/kg.

Especially preferably the (R)-dihydroetorphine is administered in a dose of 0.01 to 1 µg/kg/h, more preferably 0.02 to 0.75 µg/kg/h and still more preferably 0.03 to 0.5 µg/kg/h. Particularly preferably the (R)-dihydroetorphine is administered in a dose of 0.04 to 0.25 µg/kg/h, more preferably 0.05 to 0.175 µg/kg/h, still more preferably 0.06 to 0.16 µg/kg/h and yet more preferably 0.075 to 0.15 µg/kg/h. Still more preferably the (R)-dihydroetorphine is administered in a dose of 0.04 to 0.25 µg/kg/10 min, more preferably 0.05 to 0.175 µg/kg/10 min, still more preferably 0.06 to 0.16 µg/kg/10 min and yet more preferably 0.075 to 0.15 µg/kg/10 min.

At a dose of about 0.05 µg/kg or greater the dose response curve for analgesia is dose dependent but the dose response curve for respiratory depression or ventilation ratio is dose independent. In other words at a dose of about 0.05 µg/kg or greater the benefit from the ceiling effect in respiratory depression is realised. Thus in particularly preferred methods of the invention (R)-dihydroetorphine is administered in a dose of 0.05 to 0.175 µg/kg, more preferably 0.075 to 0.15 µg/kg, and the level of respiratory depression in the subject is between 50 and 65% relative to the baseline level pre-administration of (R)-dihydroetorphine. In further particularly preferred methods of the invention (R)-dihydroetorphine is administered in a dose of 0.075 to 0.15 µg/kg and the ventilation ratio in the subject is 0.3 to 0.5. Doses below the ceiling effect, e.g. 0.0125 µg/kg, are, however, also advantageous as the level of respiratory depression associated with these may be, e.g. as low as less than 5%.

In preferred methods of the invention, e.g. for providing anaesthesia, (R)-dihydroetorphine is administered in a dose of 0.05 to 1 µg/kg, more preferably 0.075 to 0.75 µg/kg and still more preferably 0.1 to 0.6 µg/kg. Particularly preferably the (R)-dihydroetorphine is administered in a dose of 0.15 to 0.6 µg/kg, more preferably 0.175 to 0.5 µg/kg and still more preferably 0.2 to 0.45 µg/kg. Especially preferably the (R)-dihydroetorphine is administered in a dose of 0.05 to 1 µg/kg/h, more preferably 0.075 to 0.75 µg/kg/h and still more preferably 0.1 to 0.6 µg/kg/h. Particularly preferably the (R)-dihydroetorphine is administered in a dose of 0.15 to 0.6 µg/kg/h, more preferably 0.175 to 0.5 µg/kg/h, still more preferably 0.2 to 0.45 µg/kg/h and yet more preferably 0.3 to 0.4 µg/kg/h. Still more preferably the (R)-dihydroetorphine is administered in a dose of 0.15 to 0.6 µg/kg/10 min, more preferably 0.175 to 0.5 µg/kg/10 min, still more preferably 0.2 to 0.45 µg/kg/10 min and yet more preferably 0.3 to 0.4 µg/kg/10 min. At these doses the dose response curve for analgesia is dose dependent but the dose response curve for respiratory depression or ventilation ratio is dose independent thus the benefit from the ceiling effect in respiratory depression is realised. Thus in particularly preferred methods of the invention (R)-dihydroetorphine is administered in a dose of 0.15 to 0.4 µg/kg, more preferably 0.2 to 0.3 µg/kg, and the level of respiratory depression in the subject is between 50 and 65% relative to the baseline level pre-administration of (R)-dihydroetorphine. In further particularly preferred methods of the invention (R)-dihydroetorphine is administered in a dose of 0.15 to 0.4 μg/kg and the ventilation ratio in the subject is 0.3 to 0.5.

In further preferred methods of the invention (R)-dihydroetorphine is administered in a dose greater than or equal to the $ED_{75}$ dose, more preferably a dose greater than or equal to the $ED_{85}$ dose and still more preferably a dose greater than or equal to the $ED_{90}$ dose and the level of respiratory depression in the subject is 65% or less relative to the baseline level pre-administration of (R)-dihydroetorphine. The $ED_{75}$, $ED_{85}$ and $ED_{90}$ doses may be determined by methods conventional in the art from the dose response curve, e.g. as described in the examples.

Particularly preferably (R)-dihydroetorphine is administered in a dose between the $ED_{75}$ dose and the $ED_{95}$ dose. Particularly preferably the level of respiratory depression in the subject is between 40 and 65% relative to the baseline level pre-administration of (R)-dihydroetorphine. This highlights the dose-independence of (R)-dihydroetorphine on respiratory depression. As set out above the $ED_{75}$ dose of (R)-dihydroetorphine is the dose that causes a 75% reduction in ventilation. Because respiratory depression reaches a ceiling at approximately the $ED_{50}$ dose, however, the level of ventilation at $ED_{75}$, $ED_{85}$ and $ED_{90}$ is fairly similar to that at $ED_{50}$ and is thus acceptable, e.g. around 35-50% of the baseline level. This makes the use of (R)-dihydroetorphine, particularly at higher doses, much safer to use than other opioids such as fentanyl.

Thus in one particularly preferred method of the present invention (R)-dihydroetorphine is administered in a dose greater than the $ED_{50}$ dose and less than the $ED_{75}$ dose and the level of respiratory depression in the subject is 50% or less, more preferably 45% or less and still more preferably 40% or less, relative to the baseline level pre-administration of (R)-dihydroetorphine.

In another particularly preferred method of the present invention (R)-dihydroetorphine is administered in a dose greater than the $ED_{75}$ dose and less than the $ED_{95}$ dose and the level of respiratory depression in the subject is 65% or less, more preferably 60% or less and still more preferably 55% or less, relative to the baseline level pre-administration of (R)-dihydroetorphine.

A significant advantage of the methods of the present invention is that it enables a high level of pain relief, in some cases during anaesthesia, to be provided whilst minimising risk of apnoea and the corresponding risk of need for intervention and provision of assisted breathing. This is preferably achieved by administering a dose of (R)-dihydroetorphine that provides dose dependent pain relief and dose-independent respiratory depression. Preferably the dose of (R)-dihydroetorphine achieves a $E_{MIN}$ in ventilation of 30 to 50%±10%, more preferably 35 to 45%±10% and still more preferably 35 to 45%±5%, relative to the baseline level pre-administration of (R)-dihydroetorphine. At such a dose, respiratory depression is dose-independent, but pain relief is still dose dependent. Preferably such a dose is in the range 0.075 to 0.175 μg/kg.

Preferred methods of the invention provide a level of analgesia which, as measured by the cold pressor test, is at least a −20% change, preferably at least a −40% change, more preferably at least a −50% change and yet more preferably at least a −70%, compared to baseline level, e.g. pre-administration of R-dihydroetorphine. Particularly preferred methods of the invention provide a level of analgesia which, as measured by the cold pressor test, is a −20 to −90% change, more preferably a −25 to −85% change and still more preferably a −30 to −80% change compared to baseline level, e.g. pre-administration of R-dihydroetorphine. Preferably these changes are achieved at 10 minutes, 30 minutes, 1 hour and/or 2 hours following administration of (R)-dihydroetorphine. The changes are "−" because they indicate that less pain is experienced relative to baseline level. Preferably the cold pressor test is carried out as described in the examples.

Further preferred methods of the invention increase the pain threshold level in a subject relative to the baseline level pre-administration of (R)-dihydroetorphine by at least 1.2 times and preferably at least 1.5 times. Further preferred methods of the invention increase the pain threshold level in the subject relative to the baseline level pre-administration of (R)-dihydroetorphine by 1.2 to 3.0 times. Preferably the pain threshold levels are measured by applying pain using a transcutaneous electrical stimulus to the skin over the tibial bone and increasing the electrical stimulus at a rate of 0.5 mA per 2 s, e.g. as described in the examples. Although respiratory depression is the most dangerous side effect associated with opioid pain relief treatment and anaesthesia, other side effects are also common and problematic. A benefit of the use of (R)-dihydroetorphine in the treatment of pain and provision of anaesthesia is that the spectrum of side effects associated with the treatment is minimised. In preferred methods of the invention the opioid-related side effects that are minimised. Particularly preferably the opioid related side effects are reduced compared to treatment with an equianalgesic dose of fentanyl. Preferably the opioid-related side effects that are reduced compared to an equianalgesic dose of fentanyl are selected from respiratory depression, dizziness, euphoria, nausea, sedation and dysphoria. Of these side effects, as discussed above, respiratory depression is the most dangerous since in extreme cases it can cause patient death. Thus, in particularly preferred methods of the invention, the side effect of respiratory depression is minimised, e.g. reduced.

The level of each of dizziness, euphoria, nausea, sedation and dysphoria associated with an opioid, e.g. (R)-dihydroetorphine, treatment may also be measured and quantified. This can be carried out, for example, by a questionnaire, e.g. as described in the examples herein.

In preferred methods of the invention, the side effect of dizziness is minimised. In preferred methods of the invention, the average NAS score for dizziness is 0 to 50, more preferably 0 to 45 and still more preferably 0 to 40 in the 7.5 hours post administration of (R)-dihydroetorphine.

In preferred methods of the invention, the side effect of euphoria is minimised. In preferred methods of the invention, the average NAS score for euphoria is 0 to 60, more preferably 0 to 50 and still more preferably 0 to 40 in the 7.5 hours post administration of (R)-dihydroetorphine.

In preferred methods of the invention, the side effect of nausea is minimised. In preferred methods of the invention, the average NAS score for nausea is 0 to 40, more preferably 0 to 35 and still more preferably 0 to 30 in the 7.5 hours post administration of (R)-dihydroetorphine.

In preferred methods of the invention, the side effect of sedation is minimised. In preferred methods of the invention, the average NAS score for sedation is 0 to 60, more preferably 0 to 55 and still more preferably 0 to 50 in the 7.5 hours post administration of (R)-dihydroetorphine.

In preferred methods of the invention, the side effect of dysphoria is minimised. In preferred methods of the invention, the average NAS score for dysphoria is 0 to 40, more preferably 0 to 35 and still more preferably 0 to 30 in the 7.5 hours post administration of (R)-dihydroetorphine.

In preferred methods of the invention at least two opioid-related side effects selected from respiratory depression, dizziness, euphoria, nausea, sedation and dysphoria are minimised, e.g. the average NAS scores are less than the values hereinbefore described. In particularly preferred methods at least three, and still more preferably at least four and yet more preferably all of the afore-mentioned opioid-related side effects are minimised, e.g. the average NAS scores are less than the values hereinbefore described.

In still further preferred methods respiratory depression and at least one opioid-related side effect selected from dizziness, euphoria, nausea, sedation and dysphoria are minimised, e.g. the average NAS scores are less than the values hereinbefore described. In particularly preferred methods respiratory depression and at least two, and still more preferably at least three and yet more preferably at least four of the afore-mentioned opioid-related side effects are minimised, e.g. the average NAS scores are less than the values hereinbefore described.

In a particularly preferred method of the invention, during the treating, opioid-related respiratory depression is 65% or less relative to the baseline level pre-administration of (R)-dihydroetorphine and at least one, preferably at least two, still more preferably at least three, yet more preferably at least four and even more preferably all of the following criteria defining the levels of opioid-related side effects is satisfied in the 7.5 hours post administration of (R)-dihydroetorphine:
average NAS score for dizziness of 0 to 50
average NAS score for euphoria of 0 to 60
average NAS score for nausea of 0 to 40
average NAS score for sedation of 0 to 60
average NAS score for dysphoria of 0 to 40.

In further preferred methods of the present invention, opioid-related side effects are reduced compared to the use of another opioid. In further preferred methods, the opioid-related side effects are reduced compared to the use of an equianalgesic dose of fentanyl. A reduction in side-effects compared to fentanyl is highly desirable as fentanyl is currently regarded as the gold standard opioid for treatment of pain and provision of anaesthesia.

When comparing the opioid-related side effects caused by (R)-dihydroetorphine and by another opioid, e.g. fentanyl, the comparison is between doses achieving an equivalent analgesic effect, i.e. an equianalgesic effect. Otherwise the treatments are identical, i.e. the formulation of the opioids is identical or similar, e.g. drug in aqueous solution with tonicity modifier with or without a pH buffering agent, the route of administration is identical and critically the analgesia achieved is identical.

When comparing the opioid-related side effects caused by (R)-dihydroetorphine and by another opioid, e.g. fentanyl, preferably the peak pain threshold values are preferably within ±20%, more preferably within ±10% and still more preferably within ±5%. When comparing the opioid-related side effects caused by (R)-dihydroetorphine and by another opioid, e.g. fentanyl, preferably the average pain threshold values are preferably within ±20%, more preferably within ±10% and still more preferably within ±5%.

Examples of some equianalgesic doses of (R)-dihydroetorphine and fentanyl are shown in the table below:

| (R)-Dihydroetorphine (µg/kg) | Fentanyl (µg/kg) |
| --- | --- |
| 0.0125 | 0.150 to 0.3, preferably 0.185 to 0.3, more preferably 0.225 |
| 0.075 | 0.90 to 1.875, preferably 1.125 to 1.875, more preferably 1.35 |
| 0.125 | 1.500 to 3.125, preferably 1.875 to 3.125, more preferably 2.25 |
| 0.15 | 1.800 to 3.125, preferably 2.25 to 3.75, more preferably 2.7 |

As discussed above, the level of respiratory depression associated with an opioid, e.g. (R)-dihydroetorphine and fentanyl, treatment may be measured and quantified and therefore compared. In preferred methods of the invention, the respiratory depression is less than with an equianalgesic dose of fentanyl. Particularly preferably the respiratory depression is at least 10% less, more preferably at least 20% less and still more preferably at least 30% less. In some methods of the invention, respiratory depression may be avoided altogether and is 100% less. As above, when comparing the opioid-related side effects caused by (R)-dihydroetorphine and by another opioid, e.g. fentanyl, the comparison is between doses achieving an equivalent analgesic effect.

In further preferred methods of the invention, dizziness is less than with an equianalgesic dose of fentanyl. Particularly preferably dizziness is at least 5% less, more preferably at least 10% less and still more preferably at least 15% less. In some methods of the invention, dizziness may be avoided altogether and is 100% less.

In further preferred methods of the invention, euphoria is less than with an equianalgesic dose of fentanyl. Particularly preferably euphoria is at least 5% less, more preferably at least 10% less and still more preferably at least 15% less. In some methods of the invention, euphoria may be avoided altogether and is 100% less.

In further preferred methods of the invention, nausea is less than with an equianalgesic dose of fentanyl. Particularly preferably nausea is at least 5% less, more preferably at least 10% less and still more preferably at least 15% less. In some methods of the invention, nausea may be avoided altogether and is 100% less.

In further preferred methods of the invention, sedation is less than with an equianalgesic dose of fentanyl. Particularly preferably sedation is at least 5% less, more preferably at least 10% less and still more preferably at least 15% less. In some methods of the invention, sedation may be avoided altogether and is 100% less.

In further preferred methods of the invention, dysphoria is less than with an equianalgesic dose of fentanyl. Particularly preferably dysphoria is at least 5% less, more preferably at least 10% less and still more preferably at least 15% less. In some methods of the invention, dysphoria may be avoided altogether and is 100% less.

In preferred methods of the invention at least two opioid-related side effects selected from respiratory depression, dizziness, euphoria, nausea, sedation and dysphoria are reduced compared to treatment with an equianalgesic dose of fentanyl. In particularly preferred methods at least three, and still more preferably at least four and yet more preferably all of the afore-mentioned opioid-related side effects are reduced compared to treatment with an equianalgesic dose of fentanyl.

In further preferred methods of the present invention respiratory depression and at least one opioid-related side effect selected from dizziness, euphoria, nausea, sedation and dysphoria are reduced compared to treatment with an equianalgesic dose of fentanyl. In particularly preferred methods respiratory depression and at least two, and still more preferably at least three and yet more preferably at least four, e.g. all, of the afore-mentioned opioid-related side effects are reduced compared to treatment with an equianalgesic dose of fentanyl.

In the methods of the invention, e.g. for providing pain relief, the (R)-dihydroetorphine may be administered in a variety of ways including for example regionally or systemically. The (R)-dihydroetorphine may also be administered parenterally. Preferably the (R)-dihydroetorphine is administered parenterally and more preferably intravenously.

Intravenous delivery of drugs may be carried out by either one or more bolus injections or by a continuous infusion. A bolus injection is defined herein as the injection of (R)-dihydroetorphine, preferably in a relatively high quantity, over a short period of time and is the opposite of gradual administration. Continuous infusion is defined as the administration of (R)-dihydroetorphine over a prolonged period of time.

When used for providing anaesthesia, (R)-dihydroetorphine may be administered locally or generally. Local anaesthesia includes regional, epidural and spinal anaesthesia. In the methods of the invention different types of anaesthesia may also be used in combination. For example a regional anaesthesia may be used following a general anaesthesia to relive post operative pain.

The (R)-dihydroetorphine may be formulated in a variety of ways, depending upon the route of administration selected. The quantity of (R)-dihydroetorphine in the formulation also depends upon the route of administration selected. The skilled man will readily be able to determine suitable formulations for use in the present invention.

The (R)-dihydroetorphine may be present in the form of a pharmaceutically acceptable salt. Preferred salts are those that retain the biological effectiveness and properties of (R)-dihydroetorphine and are formed from suitable non-toxic organic or inorganic acids. Acid addition salts are preferred. Representative examples of salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid and trifluoro acetic acid. The modification of a compound into a salt is a technique well known to chemists to obtain improved physical and chemical stability, hygroscopicity, flowability and solubility of compounds. Alternatively, however, (R)-dihydroetorphine is present in the form of free base.

Solutions or suspensions of (R)-dihydroetorphine used for parenteral, e.g. intravenous, administration may include one or more of the following carriers: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Preferred carriers for use in intravenous administration include physiological saline, bacteriostatic water, Cremophor EL™ (BASF, Parsippany, N.J.) or phosphate buffered saline (PBS). The composition preferably is sterile and should be fluid to the extent that easy syringability exists. The compositions are preferably stable under the conditions of manufacture and storage and preserved against the contaminating action of microorganisms such as bacteria and fungi. The carrier may be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, sorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions may be prepared by conventional procedures known in the art. In a typical procedure (R)-dihydroetorphine, in a therapeutically effective or beneficial amount, is incorporated into an appropriate solvent with one or a combination of ingredients mentioned above, as required, followed by filtered sterilization. Generally, dispersions are prepared by incorporating (R)-dihydroetorphine into a sterile vehicle which contains a basic dispersion medium and the required other ingredients from those mentioned above. In the case of sterile powders for the preparation of sterile injectable solutions, the preferred methods of preparation are vacuum drying and freeze-drying which yields a powder of (R)-dihydroetorphine plus any additional desired ingredient.

(R)-dihydroetorphine may be administered alone, or in combination with one or more other compounds. Combination therapy includes administration of a single pharmaceutical dosage formulation comprising (R)-dihydroetorphine and one or more additional active pharmaceutical ingredients, as well as administration of (R)-dihydroetorphine and each additional pharmaceutical active ingredient, in its own separate pharmaceutical dosage formulation. Where separate dosage formulations are used, (R)-dihydroetorphine and one or more additional pharmaceutical active ingredients may be administered at essentially the same time (e.g., concurrently) or at separately staggered times (e.g., sequentially).

When used in methods for providing anaesthesia, a sedative is preferably administered in addition to (R)-dihydroetorphine. The sedative may be administered simultaneously, separately or sequentially with the (R)-dihydroetorphine, but is preferably administered simultaneously. Preferably the sedative and (R)-dihydroetorphine are in separate dosage forms.

Preferred sedatives include Diprivan® (propofol or 2,6-diisopropylphenol), Lusedra® (fospropofol disodium), Pentothal® (thiopental), Precedex® (dexmedetomidine), Amidate® (etommidate), Ketalar® (ketamine), propanidid (4-[(N,N-diethylcarbamoyl)methoxy]-3-methoxyphenyl]acetic acid propyl ester), Nembutal® (pentobarbital sodium), Brevital® sodium (methohexital sodium) and valium. More preferably the sedative is propofol.

The skilled man in the art is readily able to determine appropriate doses of sedative depending on, inter alia, the weight of the patient and the level of sedation required.

In preferred methods of the invention the pain treated is acute or chronic pain. Examples of pain that may be treated include nociceptive, inflammatory, neuropathic or mixed pain. This includes visceral, somatic, radicular, neuralgic, central pain, pain associated with amputation, complex regional pain syndromes and fibromyalgia. In particularly preferred methods of the invention the pain treated is nociceptive pain. Such pain is caused by tissue injury detected by nociceptors at the site of injury. After the injury, the site becomes a source of ongoing pain and tenderness. This pain and tenderness are considered "acute" nociceptive pain. In preferred methods of the invention, acute nociceptive pain is treated. Examples of acute nociceptive pain include surgical procedures (post-op pain) and bone fractures.

Even though there may be no permanent nerve damage, "chronic" nociceptive pain results from some conditions when pain extends beyond six months. In other preferred methods of the invention chronic nociceptive pain is treated. Examples of chronic nociceptive pain include osteoarthritis, rheumatoid arthritis, and musculoskeletal conditions (e.g., back pain) and cancer pain.

The present invention will now be described with reference to the following non-limiting example wherein.

Figure 8:
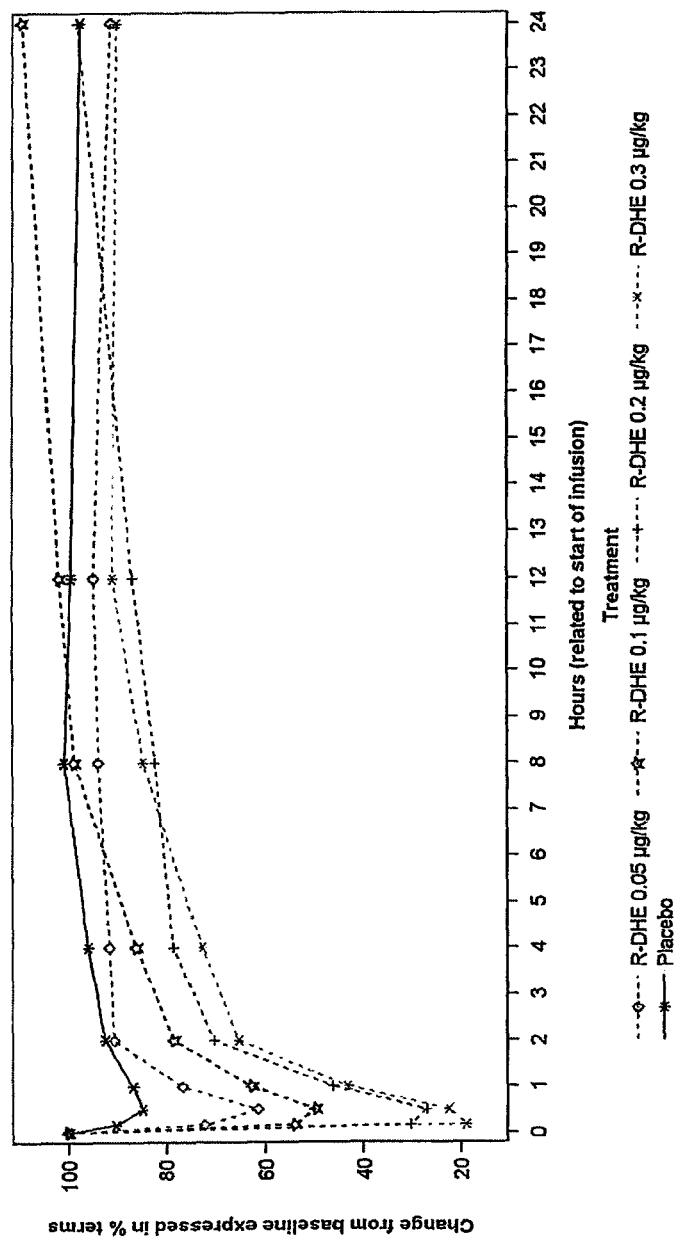

FIG. 8 shows the R-DHE dose response in the cold pressor test model for nociceptive pain FIG. 9 shows a questionnaire for completing by patients in assessing other opioid-related side effects associated with treatment of each of 0.15 µg/kg (R)-dihydroetorphine and 3 µg/kg fentanyl at intervals for 7.5 hours, starting 1 hour after administration of drug was ceased, wherein the scale 0-100 for each side effect is a NAS score.

EXAMPLES

Example 1a

In the examples R-DHE was compared to fentanyl, which is a selective and high affinity MOR agonist that produces dose-dependent respiratory depression and apnoea at high dose (2-3 µg/kg and greater). Fentanyl is currently the opioid of choice for the treatment of many types of moderate to severe pain.

Methods

The phase 1 study had two parts. Initially a dose-ascending, cohort group, single-blinded pilot study (part 1) was performed for dose-finding. After the pilot study was completed, the R-DHE doses were selected for the main study (part 2), a randomised, double-blind, placebo- and active comparator (fentanyl)-controlled study was performed. Parallel group study was performed.

Subjects

One hundred and two male healthy volunteers (10 in the pilot study and 92 in the main study) participated in the study after approval of the protocol was obtained from the Leiden University Medical Center (LUMC) Human Ethics Committee and the Central Committee on Research Involving Human Subjects (CCMO, The Hague). Written and oral informed consent was obtained prior to enrolment of the volunteers into the study. All volunteers provided a medical history and a physical examination, 12-lead ECG and blood screening was conducted before enrolment. The eligible volunteers were between the ages of 18 and 45 years, weighed between 65 and 100 kg, had a body mass index between 18 and 30 kg/m$^2$ and a forced expired lung volume in 1 s of >85% of predicted. Study subjects were healthy with no history of major medical disease, alcohol abuse, illicit drug use or heavy smoking. Volunteers had not used medication (including vitamins, herbal and/or mineral supplements) in the seven days preceding dosing, or during the course of the study, or opioids or opioid antagonists in the 90 days prior to dosing. Finally, participants had to fast for at least 6 hours prior to the administration of study medication.

Study Design

Pilot study—The respiratory effects of 3 escalating doses of R-DHE and 1 infusion of placebo were tested on 4 separate days with at least 1 week for wash out between test sessions. Three subjects received 0.025, 0.05 and 0.1 µg/kg R-DHE and placebo (cohort 1), three others 0.0125, 0.075 and 0.1 µg/kg R-DHE and placebo (cohort 2) and the last three subjects 0.05, 0.125 and 0.15 µg/kg R-DHE and placebo (cohort 3). From the results of this study the doses of the main study were determined. After infusion of the drug was completed ventilation was continuously measured breath to breath for 1 hour under iso-hypercapnic conditions (see below).

Main study—In this double-blind randomized study 92 volunteers participated. None of them had been part of the pilot study and all were dosed only once. 46 subjects participated in the respiratory part of the study and the 46 other subjects in the analgesia part. In both parts, placebo (n=6), 0.0125 µg/kg R-DHE (n=4), 0.075 µg/kg R-DHE (n=6), 0.125 µg/kg R-DHE (n=6), 0.15 µg/kg R-DHE (n=4), 0.5 µg/kg fentanyl (n=4), 1 µg/kg fentanyl (n=6), 2 µg/kg fentanyl (n=6) and 3 µg/kg fentanyl (n=4) was administered by intravenous infusion over 10 minutes. The randomization list was prepared by the sponsor of the study and sent to the local pharmacy where blinded syringes were prepared based on the weight of the subject. Each syringe was identical in size, drug volume and color and was unmarked. The randomization list was available to the sponsor, the pharmacy and an independent data safety monitoring committee.

Study Medications

Placebo was normal saline (0.9% NaCl).

Fentanyl was obtained from Hameln Pharmaceuticals (Hameln Germany).

R-DHE was manufactured by SCM Pharma Limited on behalf of Mundipharma Research Limited (Cambridge, UK).

Solutions of each of R-DHE and fentanyl were prepared by conventional techniques.

All drugs were infused intravenously (through an intravenous line in the arm or hand) using a syringe pump (Beckton Dickinson, St. Etienne, France).

Respiratory Measurements

Following infusion, ventilation was continuously measured on a breath-to-breath basis for 1 hour under iso-hypercapnic conditions. End-tidal gas forcing and data acquisition were performed using the dynamic end-tidal forcing technique. This technique is well established and is described in, inter alia, *Journal of Physiology* (1990), 428, 485-499, *PLoS Medicine* (2007), 4, e239, 1195-1203 and *British Journal of Anaesthesia* (2005), 94(6), 825-834, the entire contents of which are hereby incorporated by reference. The advantages of the end-tidal forcing technique are that respiratory response of the test drug is (1) independent of the confounding effects of changes in arterial $CO_2$ and (2) independent of the speed of administration of the drug. The technique therefore allows reliable comparison of drug effect on the ventilatory control system, i.e. differences induced by R-DHE and fentanyl in dose-response relationships are due to $CO_2$-independent differences in pharmacokinetics and dynamics.

The dynamic end-tidal forcing technique enables the investigator to force end-tidal $PCO_2$ and end tidal $PO_2$ to follow a specific pattern over time. In the current study the end-tidal oxygen ($O_2$) level was clamped to a value of 110 mmHg, while the end-tidal carbon dioxide ($CO_2$) concentration was slowly increased to a value that caused ventilation levels of 20±2 L/min. This end-tidal $CO_2$ value was maintained throughout the study. On average this was achieved by increasing end-tidal $PCO_2$ to 6.65 kPa (50 mmHg).

The volunteers were comfortably positioned in a hospital bed and breathed through a face mask positioned over their nose and mouth which was connected to a pneumotachograph and differential pressure transducer (#4813, Hans Rudolph, Myandotta, Mich.). The pneumotachograph received fresh gas from a gas-mixing system consisting of three mass flow controllers (Bronkhorst High Tech, Veenendaal, The Netherlands) for oxygen, carbon dioxide and nitrogen. A personal computer running ACQ software (Erik Kruyt, Leiden University Medical Center, Leiden, The Netherlands) provided control signals to the mass flow controllers, allowing adjustment of the inspired gas concentrations to steer the end-tidal $O_2$ and $CO_2$ concentrations according to a pre-set pattern over time. The inspired and expired oxygen and carbon dioxide concentrations and the arterial hemoglobin-oxygen saturation were measured with a Datex Multicap gas monitor (near the mouth) and Datex Satellite Plus pulse oximeter, respectively (Datex-Engstrom, Helsinki, Finland). End-tidal concentrations of oxygen and carbon dioxide, inspired minute ventilation (Vi), and oxygen saturation were collected for further analysis. Ventilation levels and end-tidal concentrations were observed in real time on a breath-to-breath basis on a computer screen.

Respiratory measurements started when the inspired minute ventilation had reached a steady state; 4-5 min later drug infusion was started. Respiratory measurements ended 65 min after the end of drug infusion (t=70 min).

Pain Measurements

Pain was induced using a transcutaneous electrical stimulus to the skin over the left tibial bone (10 cm above the ankle). A 20 Hz (pulse duration 0.1 ms) stimulus train was delivered to the subject causing activation of cutaneous nociceptors. The stimulus train started at 0 mA and was increased at a rate of 0.5 mA per 2 s (with a cut-off value of 128 mA). The delivery of the current was controlled by a computer via a current stimulator which was connected to a control box with two buttons. The subject was instructed to press the first button when pain was felt (i.e. pain threshold) and the second button when the subject wanted the stimulus train to stop (i.e. pain tolerance). These respective currents were collected on disc for further analysis. The subject was familiarized with the system prior to the study to obtain reliable baseline values. In this study, the pain threshold values were used in the analysis. Four pain threshold values (i.e. predrug values) were obtained in the 30 minutes prior to drug infusion. These values were averaged and served as a baseline estimate. Following drug infusion, pain measurements were obtained at the following time points (t=0 is the start of drug infusion): 10 (end of infusion), 15, 30, 45, 65, 75, 90, 105, 120, 150, 180, 210, 240, 300, 365, 420 and 480 min.

Sample Size and Statistical Analysis

The pilot study was designed to determine which doses of R-DHE to be tested in the main study. Four doses were chosen for the main study, 0.0125 µg/kg, 0.125 µg/kg, 0.075 µg/kg and 0.15 µg/kg.

For the main study, sample size selection was achieved by performing a power analysis in NONMEM (Beal, B. L., Sheiner, L. B., Boeckman, A. J., Bauer, R. J., User's Guide, Icon Development Solutions, Ellicott City, Md., 1989-2011) using estimated data on the effect of opioids on respiratory depression (pilot study and *Clin. Pharmacol. Ther.* 2007, 81: 50-58). An inter-subject variability in effect of 50% ($\omega^2=0.25$) and a 10% residual error for effect ($\sigma^2=0.01$) and aimed to detect a value of η<0.5 or >2 (where $C_{50A}$(R-DHE)/$C_{50R}$(R-DHE)=ρ×$C_{50A}$(FENTANYL)/$C_{50R}$(FENTANYL) and $C_{50A}$ and $C_{50R}$ are the concentrations causing 50% analgesia and respiratory depression for drugs R-DHE (R-DHE) and fentanyl (FENTANYL), respectively) with α<0.05 and β=0.8. In the analysis we assumed that $C_{50A}$(R-DHE)=$C_{50A}$(FENTANYL) (i.e. concentrations are equianalgesic). Values of ρ<0.5 indicated that fentanyl produces respiratory depression at concentrations at least twice as low as R-DHE and vice versa for ρ>2. It was assumed that the logarithm of the $C_{50}$ ratio has a normal distribution with variance=1. The sample size selection was then verified by simulations in NONMEM with 1,000 simulated data sets. The analysis resulted in a sample size of 34, which was rounded upwards to 40 (20 subjects per opioid treatment). Six additional subjects were added to receive placebo. The subject number chosen for the analgesia part of the study was identical to that calculated for the respiratory part of the study.

Average Respiratory Drug Effect

Figure 1:
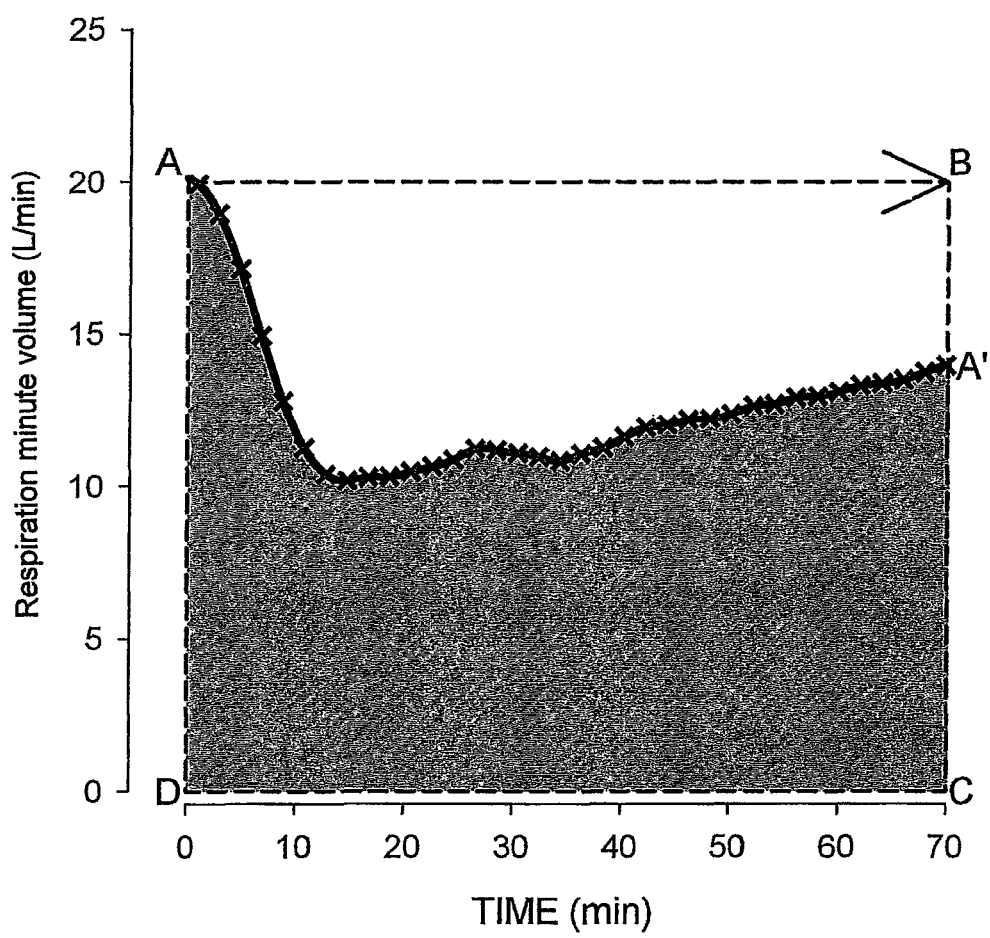
FIG. 1 illustrates calculation of average respiratory drug effect.

The breath-to-breath data were averaged over 1-min episodes. In order to get an impression of the average drug effect on respiration, we calculated the area below the respiration curve (AUC) from t=0 to t=70. Referring to FIG. 1, first the area-under-the curve (AUC) was calculated for the respiration curve (blue line from A to A'). This AUC (grey field) was subtracted from the area obtained by taking baseline ventilation (A) forward (the arrow from point A to B; the baseline area AUC is the box depicted by the red broken lines ABCD). Next the data were normalized by the baseline area giving an average % of respiratory depression (average drug effect=[baseline area AUC−AUC]/baseline area AUC An average drug effect of 40 indicates an average of 40% respiratory depression over the measured time period (0-70 min). The average drug effect and time to peak effect were analyzed using a one-way analysis of variance (factor dose). The R-DHE and fentanyl data were analyzed separately in Sigmaplot v12.3 (Systat Software GmbH, Ekrath, Germany). P-values <0.05 were considered significant. Values given are mean±SD.

Peak Respiratory Depression

For each subject peak respiratory depression was calculated as the nadir in ventilation and presented as ratio relative to baseline (e.g. a value of 0.5 indicates a nadir in ventilation in magnitude 50% of baseline ventilation). Using the statistical package R (version 8.2; www.r-project.org), a sigmoid E function was fitted through the R-DHE and fentanyl dose-effect data (effect=peak respiratory depression) using a model of the form:

$$\text{Peak effect(dose)}=100+[E_{MIN}-100]\times[\text{dose}^\gamma \div ED_{50}^\gamma]\qquad\text{eqn. (1)}$$

where $ED_{50}$ is the dose causing a 50% effect (ventilation in the middle of baseline ventilation and $E_{MIN}$), $E_{MIN}$ the asymptotic minimum in ventilation, and γ a shape parameter. P-values <0.01 were considered significant. The data analysis was performed on the complete data set (fentanyl data and R-DHE data from pilot and main studies). The data are presented as mean±SD.

Analgesic Effect

Two measures of analgesic effect were calculated in each experiment: peak analgesia (defined as the highest value of pain threshold in mA) and average analgesic effect (as defined as the area under the pain threshold curve from t=0 to t=8 h normalised by the baseline area, see above). Peak and average analgesic effects were analyzed using a one-way analysis of variance (factor dose). The R-DHE and fentanyl data were analyzed separately using SigmaPlot v 12.3. P-values <0.05 were considered significant. Values given are mean±SD.

Results

Pilot study—Nine volunteers completed the study without unexpected side effects. One subject developed ECG changes that, although not clinically relevant, precluded proper assessment of the effect of the study medication on the ECG. As a precautionary measure, another subject replaced this subject after having completed a placebo and 0.05 μg/kg R-DHE experiment.

Figure 2:
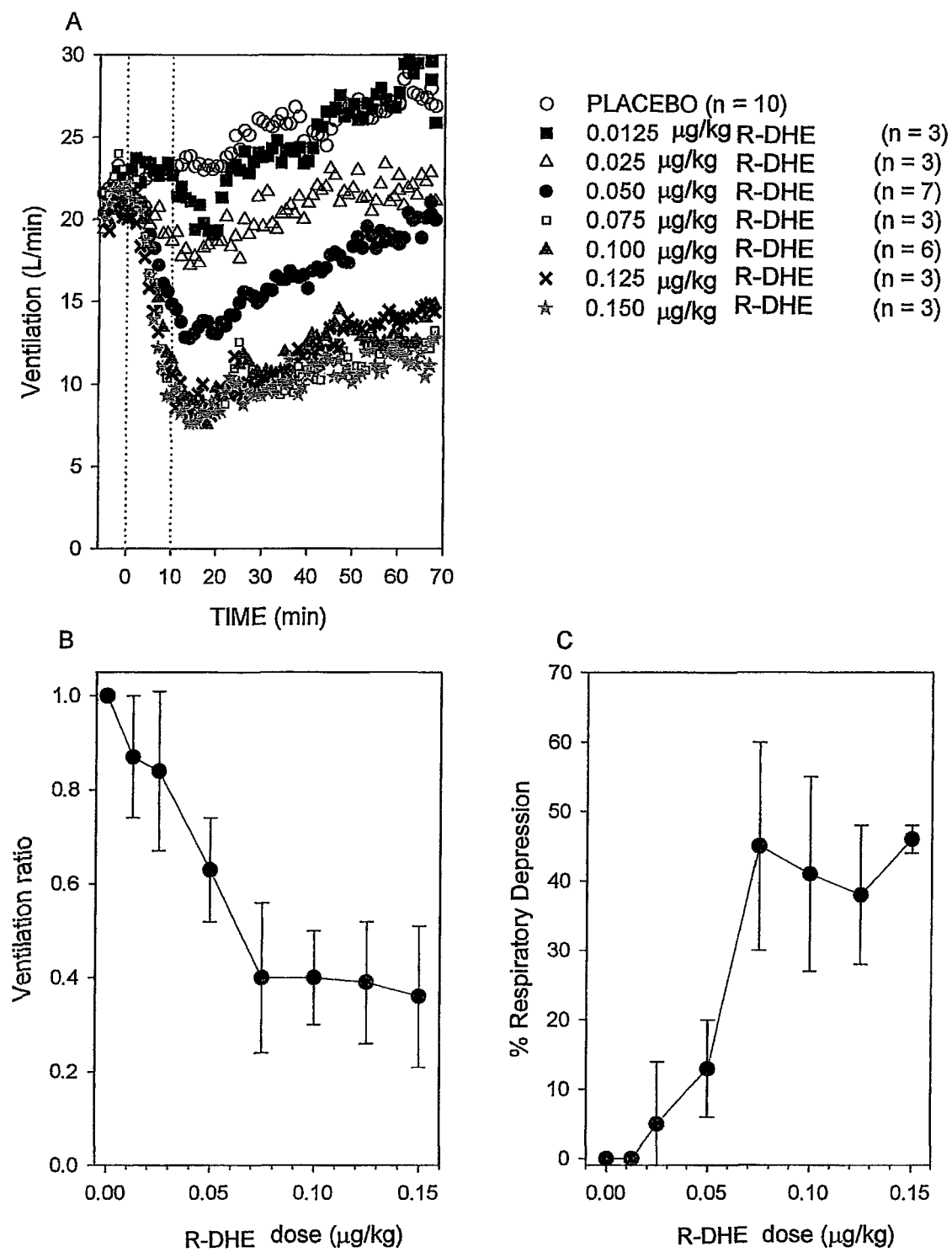
FIG. 2a shows the plots of ventilation (L/min) versus time in the pilot study for placebo and eight R-DHE dosages.
FIG. 2b shows a plot of ventilation ratio versus R-DHE dose in the pilot study (The data in panel B are mean±SD)
FIG. 2c shows a plot of % respiratory depression versus R-DHE dose in the pilot study (The data in panel C are mean±SD)

The clamped end-tidal $PCO_2$ was 6.6±0.5 kPa (49.5±3.8 mmHg) and baseline (pre-drug) ventilation was 21.5±1.7 L/min. The mean respiratory responses to R-DHE are given in FIG. 2A. All dosages of R-DHE displayed a nadir in ventilation, which occurred at t=17.1±3.8 min following the start of drug infusion. The respiratory responses to R-DHE dosages of 0.075, 0.10, 0.125 and 0.15 μg/kg overlap. The dose-response curves (peak respiratory depression and average drug effect) are given in FIGS. 2B and C showing that the dose-response levels off at dosages of 0.075 μg/kg and greater (R-DHE 0.075, 0.125 and 0.15 μg/kg: P>0.05). The peak respiratory depression occurred with doses of 0.075 μg/kg and greater at a ventilation ratio of about 0.4. The average % respiratory depression reached a ceiling of about 40-45% with doses 0.075 μg/kg and greater. With a 40-45% average respiratory depression, the average level of respiration achieved in the volunteer who received the drug was 55-60% relative to baseline.

A small positive trend was observed in the ventilation data as was best observed in the placebo responses. The magnitude of the trend ranged from 30-60 ml·min$^{-2}$ (about 1.5-3% of total ventilation) and corresponds with the presence of a slow component (time constant about 1 hr) in the ventilatory response to $CO_2$.

Figure 3:
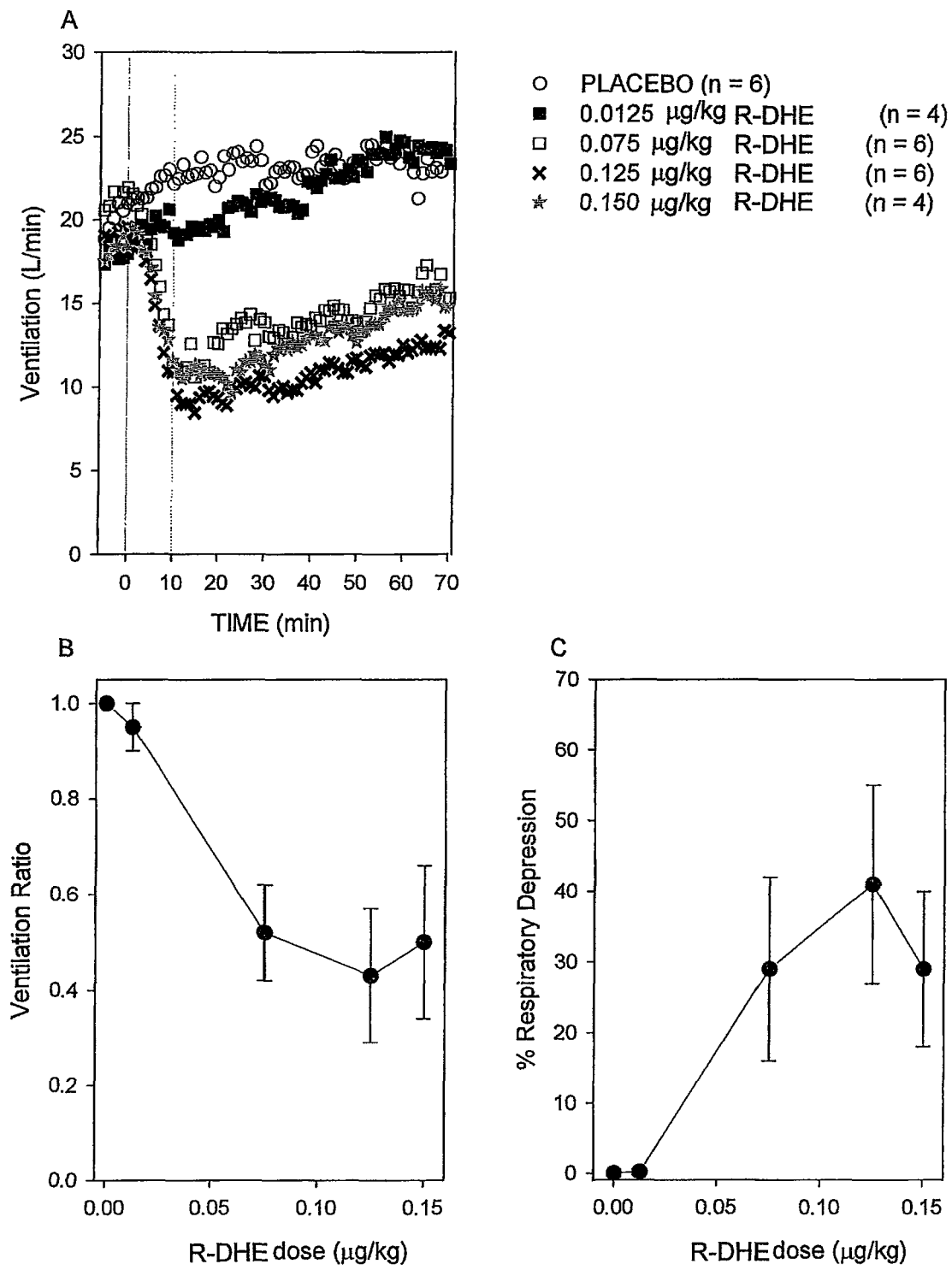
FIG. 3a shows the plots of ventilation (L/min) versus time in the main phase of the study for placebo and four R-DHE dosages.
FIG. 3b shows a plot of ventilation ratio versus R-DHE dose in the main phase of the study (The data in panel B is mean±SD)
FIG. 3c shows a plot of % respiratory depression versus R-DHE dose in the main phase of the study (The data in panel C is mean±SD)

Main study: Respiration. All 46 subjects completed the study without unexpected side effects. In the R-DHE experiments, the end-tidal $PCO_2$ was clamped at 6.8±0.2 kPa (51.0±1.5 mmHg) and baseline (pre-drug) ventilation was 19.3±1.4 L/min. The mean respiratory responses to R-DHE are given in FIG. 3A. No nadir in ventilation was observed in the placebo data and the lowest R-DHE dose tested. The time to peak effect was dose-independent and occurred at 17.3±5.5 min. The dose-response curves (for peak respiratory depression and average drug effect) are given in FIGS. 3B and C respectively showing that the dose-response levels off at a ventilation level of approximately 40% of baseline. Specifically the peak respiratory depression occurred with doses of 0.075 μg/kg and greater and at a ventilation ratio of about 0.5. The average % respiratory depression reached a ceiling of about 30-40% with doses 0.075 μg/kg and greater. With a 30-40% average respiratory depression, the level of respiration achieved in the volunteer who received the drug was 60-70% relative to baseline. None of the subjects that received R-DHE developed irregular breathing or apnoea.

Figure 4:
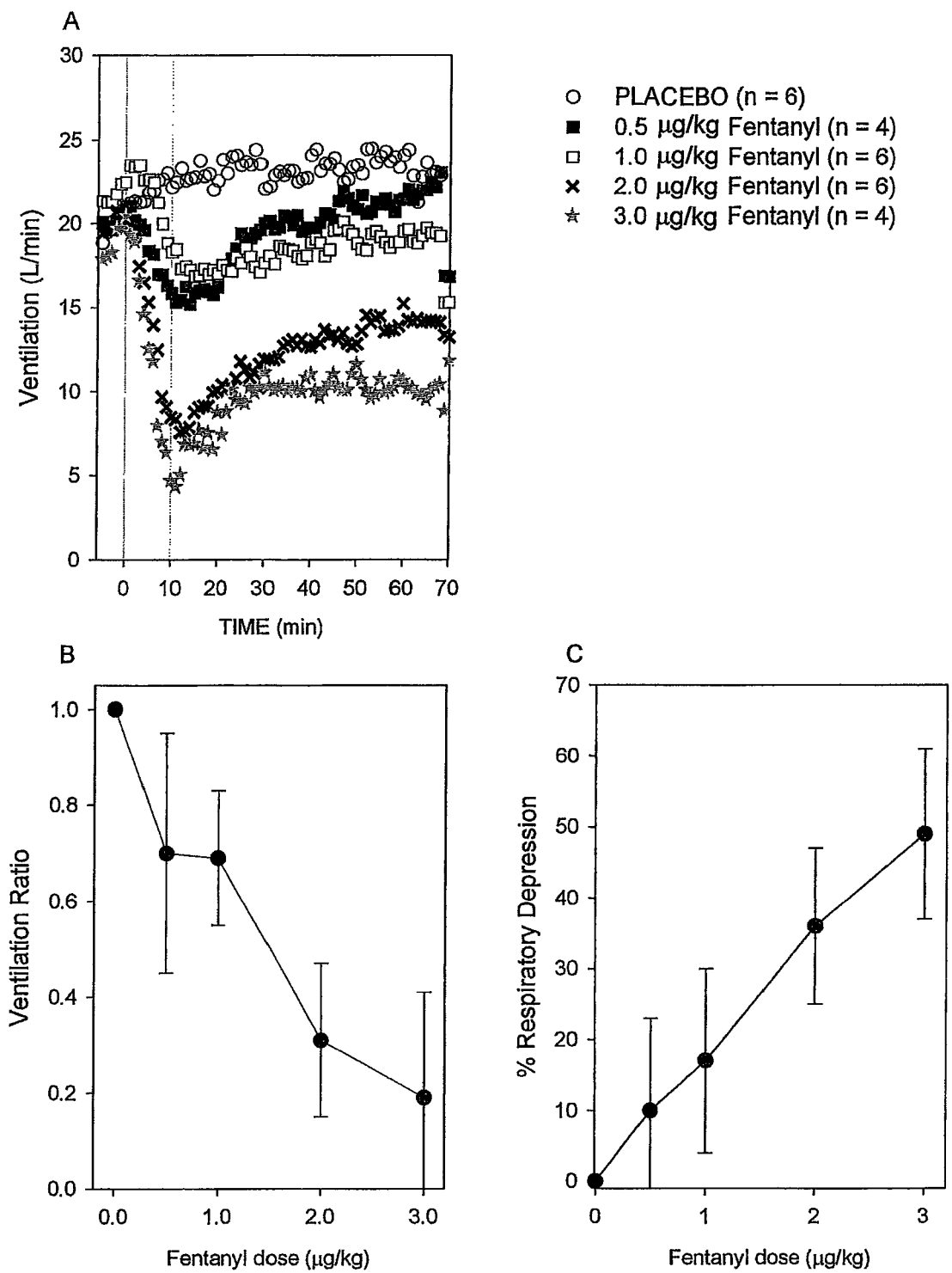
FIG. 4a shows the plots of ventilation (L/min) versus time in the main phase of the study for placebo and four fentanyl dosages.
FIG. 4b shows a plot of ventilation ratio versus fentanyl dose in the main phase of the study (The data in panel B is mean±SD)
FIG. 4c shows a plot of % respiratory depression versus fentanyl dose in the main phase of the study.

In the fentanyl experiments, the end-tidal $PCO_2$ was clamped at 6.6±0.1 kPa (49.5±0.8 mmHg) and baseline (pre-drug) ventilation was 20.2±0.9 L/min. A nadir in respiratory response was observed for all doses tested (FIG. 4A). The time to peak effect was dose-independent and occurred on average at 12.8±2.1 min. The dose-response curves (for peak respiratory depression and average drug effect) are given in FIGS. 4B and C respectively. Dose-dependent respiratory depression was apparent in peak ventilation (P<0.001) and average drug effect (P<0.001). The maximum observed respiratory depression was observed at the highest fentanyl dose tested (3 μg/kg; peak effect=19% of baseline).

Two subjects developed irregular breathing after the highest dose of fentanyl, one of which developed apnoea (defined by the absence of breathing activity >20 s), just after ending the 10-min fentanyl infusion.

The parameter estimates of the model analysis of peak respiratory depression are given in Table 1 below.

TABLE 1

Parameter estimates of the model analysis of peak respiratory depression

| Parameter | Mean | SD | 2.5% percentile | 97.5% percentile |
|---|---|---|---|---|
| $ED_{50}$ R-DHE (µg/kg) | 0.04 | 0.009 | 0.026 | 0.06 |
| $ED_{50}$ Fentanyl (µg/kg) | 1.27 | 0.116 | 1.04 | 1.50 |
| γ | 1.80 | 0.32 | 1.23 | 2.51 |
| $E_{MIN}$ R-DHE (% of baseline) | 32.8 | 0.06 | 16.7 | 42.6 |
| $E_{MIN}$ Fentanyl | 0 | — | — | — |
| $\sigma^2$ | 0.014 | 0.002 | 0.010 | 0.019 |

$ED_{50}$ is the dose causing a 50% reduction in ventilation, $E_{MIN}$ the asymptotic minimum in ventilation, γ a shape parameter and $\sigma^2$ is the variance of the residual error.

Figure 5:
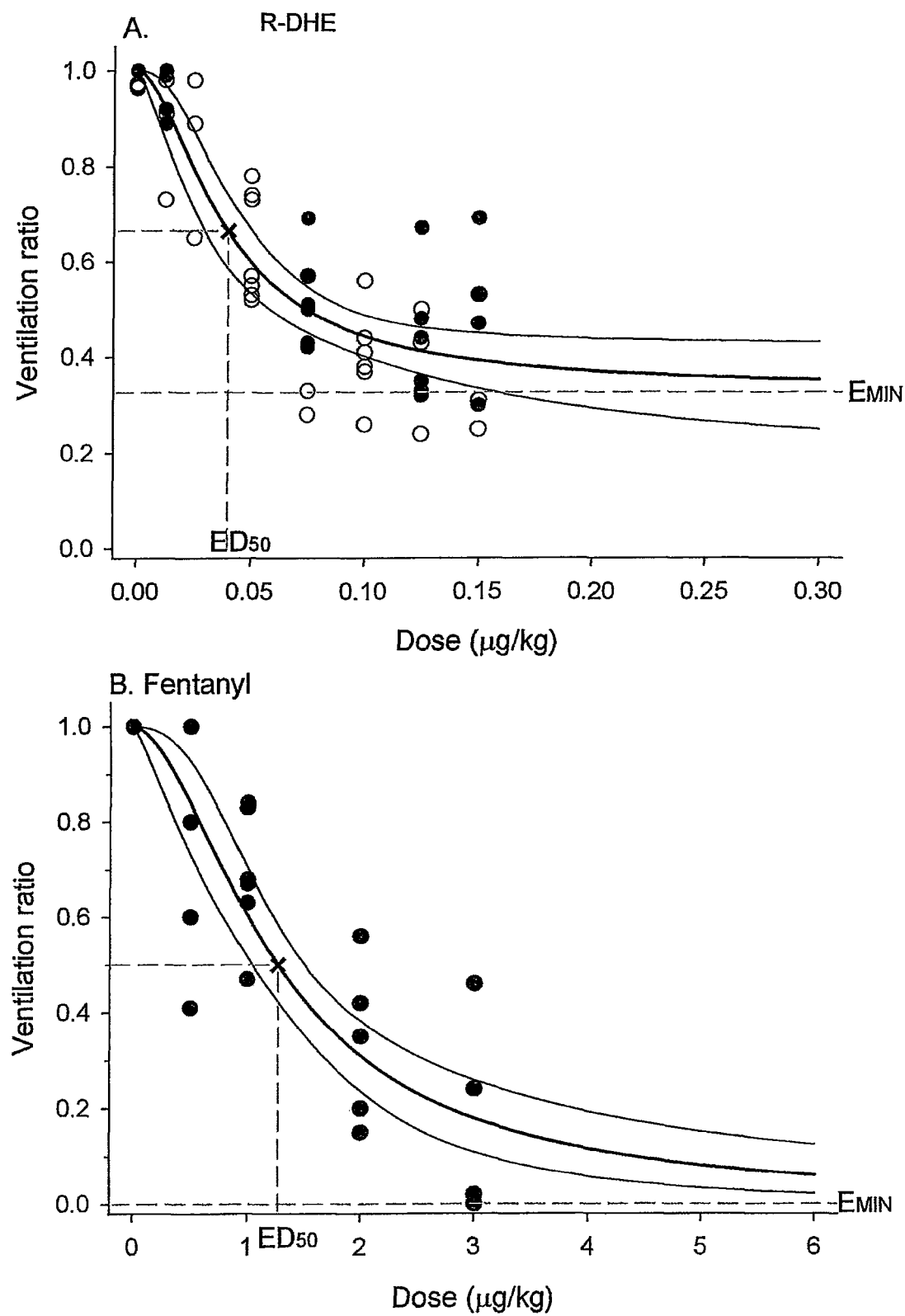
FIG. 5 shows model fits of ventilation ratio versus dose for R-DHE (A) and fentanyl (B)

The model fits are given in FIGS. 5A (R-DHE) and B (fentanyl). On the y-axis, ventilation is relative to pre-drug baseline ventilation. The continuous thick lines are the model fits and the thin lines are the 2.5% and 97.5% percentiles. The curves are extrapolated to 0.3 µg/kg (R-DHE) and 6 µg/kg (fentanyl). In panel A, the closed circles are data from the main study, the open circles are data from the pilot study. In panels A and B, the respective $ED_{50}$ and $E_{MIN}$ values are depicted by the symbol × and broken grey lines. For both drugs the $ED_{50}$ is the dose half-way between baseline ventilation and $E_{MIN}$; for fentanyl this is at 50% respiratory depression, for R-DHE at 33.6%

Two parameters were significantly different between treatments (P<0.01): $ED_{50}$ and $E_{MIN}$. An apparent 30-fold difference in potency was observed with $ED_{50}$ values of 0.04 µg/kg for R-DHE and 1.27 µg/kg for fentanyl. For fentanyl the value of $E_{MIN}$ or the asymptotic minimum ventilation was not different from zero, but greater than zero for R-DHE: 32.8% of baseline ventilation or 6.6 L/min (P<0.01). The shape parameter γ and residual error variance ($\sigma^2$) did not differ between treatments.

Main study: Analgesia—All 46 subjects completed the study without unexpected side effects. Baseline pain thresholds were 11.8±0.9 mA (R-DHE), 12.7±0.4 mA (fentanyl) and 11.0±0.6 mA (placebo). The effect of placebo was limited with an effect no greater than 10% of baseline. Both R-DHE and fentanyl produced dose-dependent effects in terms of peak analgesic effect and average drug effect (FIGS. 6A and B; drug-effect: P<0.01) with no indication of reaching a ceiling.

Figure 6:
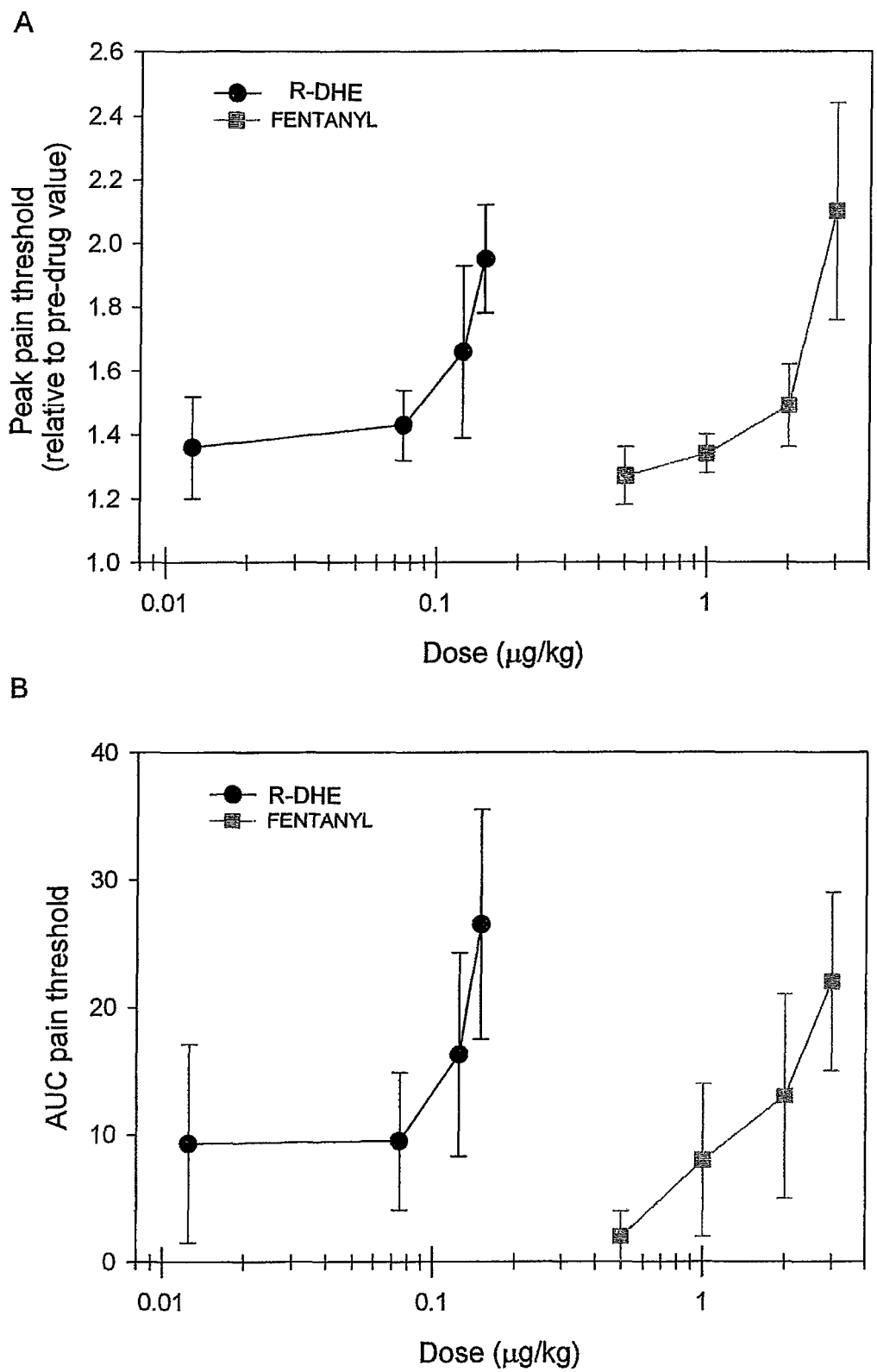
FIG. 6a shows the effect of R-DHE and fentanyl on peak analgesia, defined as the highest value of pain threshold in mA.
FIG. 6b shows the effect of R-DHE and fentanyl on average analgesic effect, defined as the area under the pain threshold curve (AUC) from t=0 to t=8 h normalised by the baseline area.
Figure 7A:
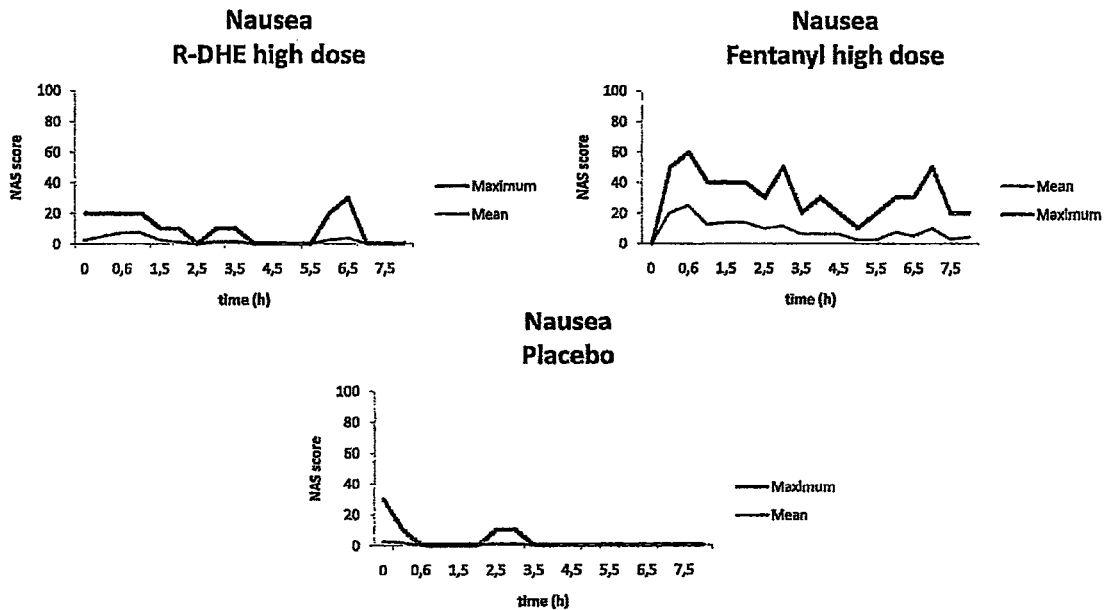
FIG. 7a shows the maximum and mean NAS scores for nausea during pain relief treatment with each of a dose of 0.15 µg/kg (R)-dihydroetorphine, 3 µg/kg fentanyl and placebo.
Figure 7B:
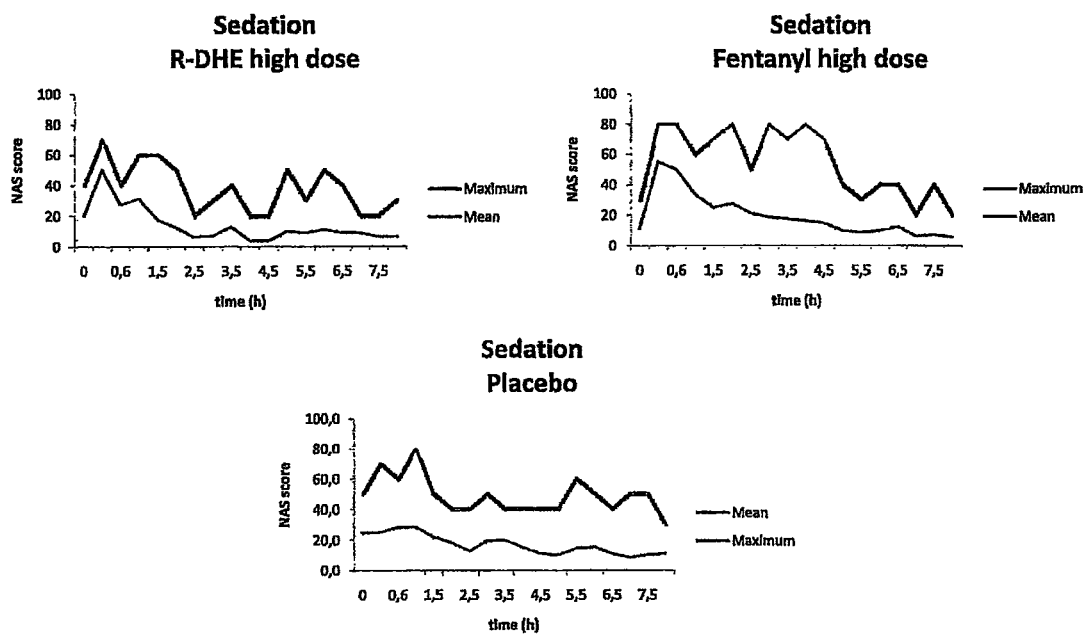
FIG. 7b shows the maximum and mean NAS scores for sedation during pain relief treatment with each of a dose of 0.15 µg/kg (R)-dihydroetorphine, 3 µg/kg fentanyl and placebo.
Figure 7C:
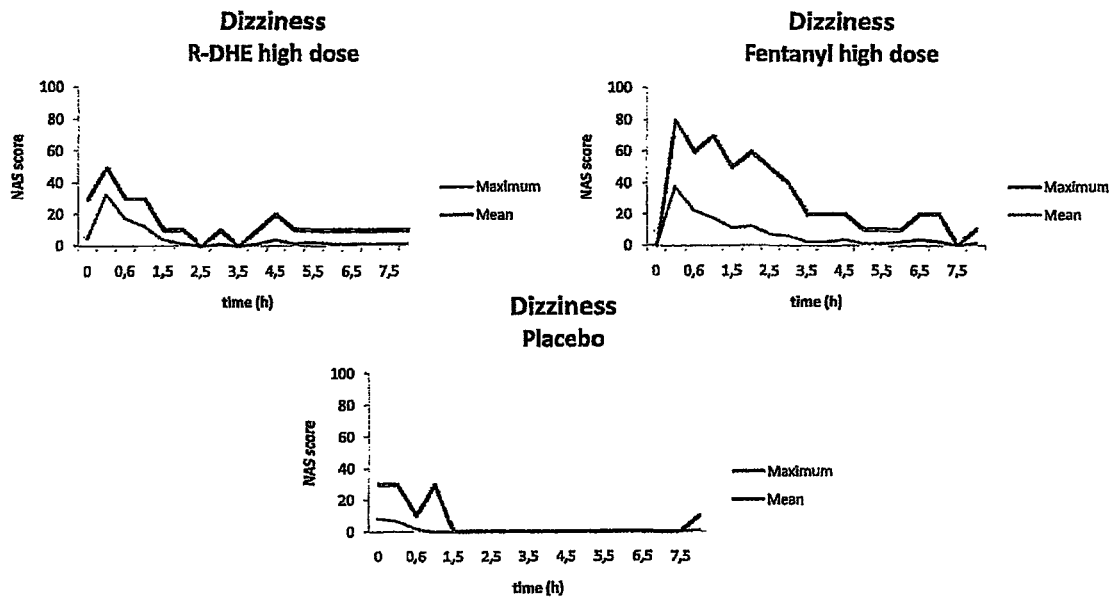
FIG. 7c shows the maximum and mean NAS scores for dizziness during pain relief treatment with each of a dose of 0.15 µg/kg (R)-dihydroetorphine, 3 µg/kg fentanyl and placebo.
Figure 7D:
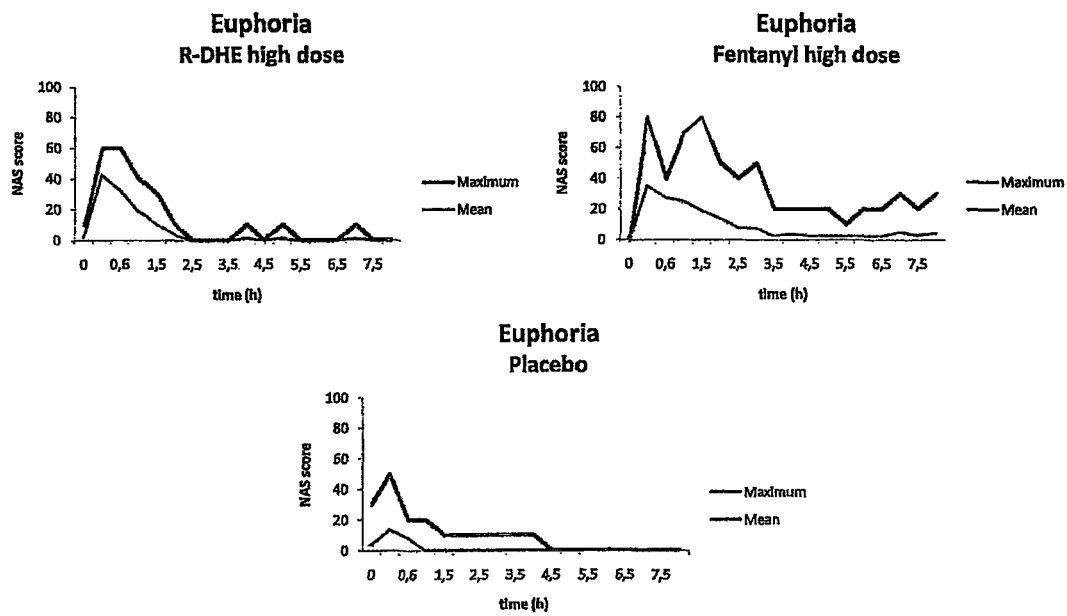
FIG. 7d shows the maximum and mean NAS scores for euphoria during pain relief treatment with each of a dose of 0.15 µg/kg (R)-dihydroetorphine, 3 µg/kg fentanyl and placebo.
Figure 7E:
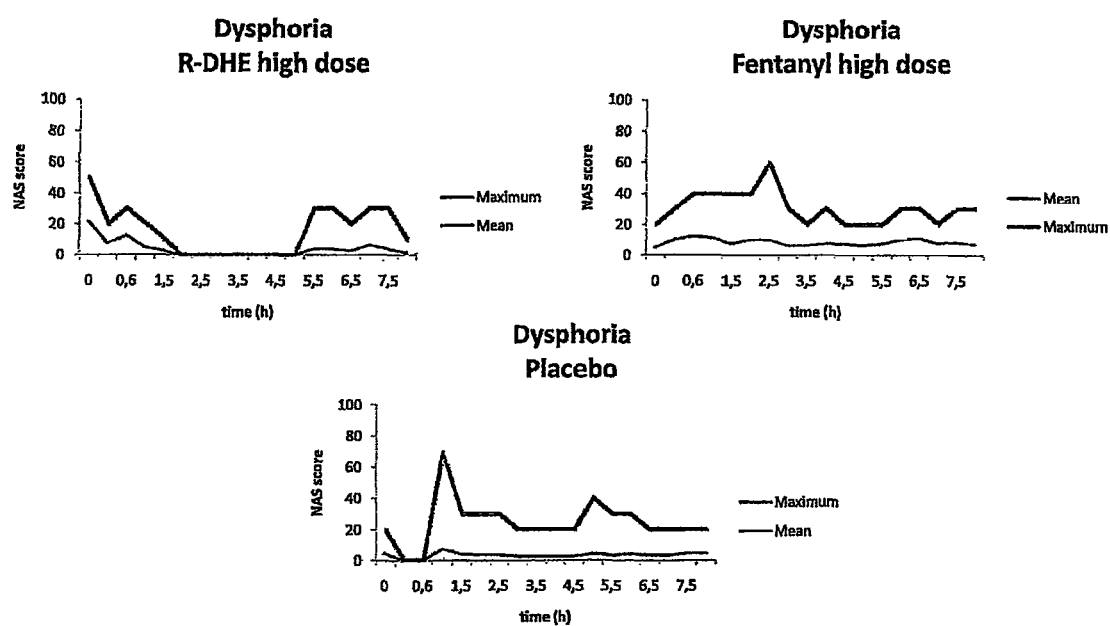
FIG. 7e shows the maximum and mean NAS scores for dysphoria during pain relief treatment with each of a dose of 0.15 µg/kg (R)-dihydroetorphine, 3 µg/kg fentanyl and placebo.

In our study we observed that over the dose range tested, both fentanyl and R-DHE displayed a dose-dependent increase in peak pain response and average analgesic effect (FIGS. 6A and B). These data provide proof that for R-DHE, in contrast to respiration, pain relief does not display ceiling over the dose range tested. At the highest dose tested both drugs produced an increase in pain threshold of about 100% (R-DHE 0.15 µg/kg response=1.95×pre-drug response; Fentanyl 3.0 µg/kg response=2.1×pre-drug response). This indicates a R-DHE-fentanyl difference in potency of 18.5. This difference is smaller than the apparent potency difference observed for respiratory depression (factor=30). However, since the $ED_{50}$ is an estimation of ventilation in the middle of baseline ventilation and $E_{MIN}$, a better comparison than $ED_{50}$ would be the dose causing 50% depression of ventilation (in absolute values). For fentanyl this is identical to $ED_{50}$ (1.27 µg/kg), and for R-DHE this is 0.075 µg/kg.

This then suggests a potency difference of 17 very similar to the value observed for antinociception.

The mechanism responsible for achieving ceiling effect is not clear. On possibility is that concurrent activation of ORL1-receptors compromises the MOR-mediated antinociceptive effect. However although R-DHE has affinity for the ORL1 receptor, its Ki is several orders of magnitude higher than for the MOR. Whether such low affinity for the ORL1 receptor is sufficient to cause the profound ceiling observed is questionable. Another possible mechanism may be related to R-DHE's high affinity for the KOR, which is approximately 1 order of magnitude lower than for the MOR. It may be, for example, that at high doses the R-DHE-induced and MOR-mediated respiratory depression is antagonised by the effect of R-DHE at the KOR.

A final proposed mechanism involves the intra neuronal regulatory protein β-arrestin. Opioid receptors belong to the 7-transmembrane G-protein-coupled receptors that, upon activation, bind to intracellular G-proteins and β-arrestin 1 and/or β-arrestin 2 proteins. It has been shown that absence of β-arrestin 2 protein causes the attenuation of morphine-induced respiratory depression with maintained antinociception. It was hypothesized that (G-protein independent) activation of β-arrestin 2 is involved in MOR signal transduction of respiratory neurons but not in neurons involved in modulation of pain pathways. It may well be that extent of G protein and of β-arrestin 2 activation is ligand specific. The findings in this study may be explained by a lesser ability of R-DHE to activate β-arrestin 2.

The mechanism of the differential R-DHE effect on respiration and analgesia is also not clear. It may be due to a difference in receptor density at brain sites involved in analgesia versus brain sites involved in respiratory depression. Another mechanism involved may be the lesser ability of R-DHE to engage the transduction protein β-arrestin 2, as discussed above. This latter mechanism explains both the observed ceiling effect in R-DHE-mediated respiratory depression and the selectivity of the ceiling effect.

Other Opioid-Related Side Effects

Other opioid-related side effects associated with treatment of each of 0.15 µg/kg (R)-dihydroetorphine and 3 µg/kg fentanyl were assessed at intervals for 7.5 hours, starting 1 hour after administration of drug was ceased, by asking the patients to complete the questionnaire shown in FIG. 9 wherein the scale 0-100 for each side effect is a NAS score. The average NAS score for each side effect was calculated.

Example 1b

In a follow up study the effect of higher doses of R-DHE were investigated. The study was conducted on 19 healthy volunteers.

The selection of subjects, formulation of R-DHE, administration (10 min i.v.), respiratory measurements (using the dynamic end-tidal forcing technique) and statistical analysis was identical to the main study described above, except that the doses of R-DHE tested were 0.2 µg/kg (6 subjects), 0.25 µg/kg (6 subjects), 0.3 µg/kg (6 subjects) and 0.4 µg/kg (6 subjects).

The ventilation ratio determined for each drug dose is shown in the table below.

| Dose of R-DHE (µg/kg) | Ventilation Ratio |
|---|---|
| 0.2 | 0.4 |
| 0.25 | 0.25 |
| 0.3 | 0.25 |
| 0.4 | 0.2 |

These results show that the ceiling effect in respiratory depression extends to higher doses of R-DHE than are required to achieve clinically useful analgesic levels. At a dose of 0.2 µg/kg of R-DHE the level of respiration in the volunteers was still about 40%. At higher doses (0.3 µg/kg and 0.4 µg/kg) an increase in peak mean respiratory depression was observed but this was stable at about 20 to 25%. Such levels are acceptable in controlled environments.

Example 2

Cold Pressor Test to Determine Analgesic Effect

The cold pressor test is an established model for nociceptive pain assessment in healthy volunteers. The test was carried out according to conventional procedures.

The R-DHE doses tested in the cold pressor model were 0.05 µg/kg (8 subjects), 0.1 µg/kg (8 subjects), 0.2 µg/kg (8 subjects) or 0.3 µg/kg (8 subjects) or placebo, all given as a 10 minute i.v. infusion.

In the study, the healthy volunteers immersed their non-dominant hand in a stirred, thermostatically-controlled cold water bath having a temperature of 3° C. for 2 minutes. During the immersion the volunteer rated the pain he or she experienced continuously with 0 representing no pain and 100 representing the worst pain imaginable. The volunteer also rated the pain experienced at time points (pre-dose, 10 minutes, 30 min, 1, 2, 4, 8, 12 and 24 hours post-infusion. The cumulative area under the curve of the visual analogue scale-time profile from 0 to 120 seconds for each cold pain test was calculated. A graph of the AUC versus baseline was plotted for each time point.

The % change from baseline was calculated as follows: 100×(AUC at t (time) with drug-AUC at t (same time) baseline/AUC at t baseline) and the results are shown in FIG. 8. Thus, for example, if the AUC for baseline was 100 and the AUC at time 10 minutes for R-DHE was 20, then the % change from baseline is 100×((20−100)/100), i.e. −80%. This is plotted on FIG. 8 as 20%. Similarly if the AUC for baseline was 100 and the AUC at time 10 minutes for R-DHE was 80, then the % change from baseline is 100×((80−100)/100), i.e. −20% and this is plotted on FIG. 8 as 80%. Thus in FIG. 8, 100% shows that no pain relief versus baseline is achieved and 0% shows that complete pain relief is achieved.

FIG. 8 shows that for a dose of R-DHE of 0.05 µg/kg, 0.1 µg/kg, 0.2 µg/kg or 0.3 µg/kg significant levels of analgesia are achieved. Significantly FIG. 8 shows that the level of analgesia achieved is dose dependent. In other words, FIG. 8 shows that, unlike for respiratory depression, no ceiling effect in analgesia is observed.

The results for placebo shown in FIG. 8 are a change from the baseline of approximately 18%, which is in line with the expected value of about 20%. Notably the results for R-DHE are significantly greater than a 20% change from baseline and for the higher doses of R-DHE (0.2 µg/kg or 0.3 µg/kg) are greater than 50% of baseline, even 1 hour after administration. Even at 4 hours after administration, the higher doses of R-DHE (0.2 µg/kg or 0.3 µg/kg) show a change from baseline that is significantly greater than the placebo.

The invention claimed is:

1. A method of providing pain relief in a human subject in need thereof comprising administering (R)-dihydroetorphine to said subject, wherein said (R)-dihydroetorphine is administered intravenously in a dose of 0.075 to 0.15 µg/kg, wherein said dose provides a level of respiratory depression in said subject of 65% or less relative to a baseline level pre-administration of (R)-dihydroetorphine.

2. The method as claimed in claim 1, wherein the level of respiratory depression in said subject provided by said dose is between 20 and 65% relative to the baseline level pre-administration of (R)-dihydroetorphine.

3. The method as claimed in claim 1, wherein said respiratory depression is the average respiratory depression measured under iso-hypercapnic conditions for 1 hour following administration of said dose of (R)-dihydroetorphine intravenously over 10 minutes.

4. The method as claimed in claim 1, wherein said method increases a pain threshold level in said subject relative to a baseline level pre-administration of (R)-dihydroetorphine by at least 1.2 times.

5. The method as claimed in claim 1, wherein the pain is nociceptive pain.

6. A method of providing pain relief in a human subject in need thereof comprising administering (R)-dihydroetorphine to said subject, wherein said (R)-dihydroetorphine is administered intravenously in a dose of 0.075 to 0.15 µg/kg, wherein said dose provides a peak respiratory depression in said subject of 20 to 80% relative to a baseline level pre-administration of (R)-dihydroetorphine.

7. The method as claimed in claim 6, wherein the peak respiratory depression in said subject provided by said dose is 30 to 40% relative to the baseline level prior to administration of (R)-dihydroetorphine.

8. The method as claimed in claim 6, wherein the peak respiratory depression is measured under iso-hypercapnic conditions for 1 hour following administration of said dose of (R)-dihydroetorphine intravenously over 10 minutes.

9. The method as claimed in claim 6, wherein said method increases a pain threshold level in said subject relative to a baseline level pre-administration of (R)-dihydroetorphine by at least 1.2 times.

10. The method as claimed in claim 6, wherein the pain is nociceptive pain.

11. A method of providing pain relief in a human subject in need thereof comprising administering (R)-dihydroetorphine to said subject, wherein said (R)-dihydroetorphine is administered intravenously in a dose of 0.075 to 0.15 µg/kg, wherein said dose provides a ventilation ratio in said subject of at least 0.3.

12. The method as claimed in claim 11, wherein the ventilation ratio in said subject is between 0.3 and 0.6.

13. The method as claimed in claim 11, wherein the ventilation ratio in said subject is 0.3 to 0.5.

14. The method as claimed in claim 11, wherein the ventilation ratio is determined by measuring respiration pre-administration of (R)-dihydroetorphine and measuring respiration for 1 hour under iso-hypercapnic conditions post-administration of said dose of (R)-dihydroetorphine, wherein the (R)-dihydroetorphine is administered intravenously over 10 minutes.

15. The method as claimed in claim 11, wherein said method increases a pain threshold level in said subject relative to a baseline level pre-administration of (R)-dihydroetorphine by at least 1.2 times.

16. The method as claimed in claim 11, wherein the pain is nociceptive pain.

17. A method of providing pain relief in a human subject in need thereof whilst minimising risk of apnoea comprising administering (R)-dihydroetorphine to said subject, wherein a dose of (R)-dihydroetorphine that provides dose dependent pain relief and dose-independent respiratory depression is administered, wherein said (R)-dihydroetorphine is administered intravenously in a dose of 0.075 to 0.15 µg/kg.

18. The method as claimed in claim 17, wherein a level of respiratory depression in said subject provided by said dose is between 40 and 65% relative to a baseline level pre-administration of (R)-dihydroetorphine.

19. The method as claimed in claim 17, wherein the level of respiratory depression in said subject provided by said dose is between 30 and 50% relative to the baseline level pre-administration of (R)-dihydroetorphine.

20. The method as claimed in claim 17, wherein said respiratory depression is the average respiratory depression measured under iso-hypercapnic conditions for 1 hour following administration of said dose of (R)-dihydroetorphine intravenously over 10 minutes.

21. The method as claimed in claim 17, wherein said method increases a pain threshold level in said subject relative to a baseline level pre-administration of (R)-dihydroetorphine by at least 1.2 times.

22. The method as claimed in claim 17, wherein the pain is nociceptive pain.

23. A method of providing pain relief in a human subject in need thereof comprising administering (R)-dihydroetorphine to said subject intravenously in a dose of 0.075 to 0.15 µg/kg, wherein said dose provides reduction in at least one opioid-related side effect when compared to the effect of a treatment with an equianalgesic dose of fentanyl.

24. The method as claimed in claim 23, wherein said opioid-related side effect is selected from the group consisting of respiratory depression, dizziness, euphoria, nausea, sedation and dysphoria.

25. The method as claimed in claim 24, wherein said opioid-related side effect provided by said dose is respiratory depression and said respiratory depression is 0 to 65%.

26. The method as claimed in claim 24, wherein said opioid-related side effect provided by said dose is respiratory depression and said respiratory depression is an average respiratory depression measured under iso-hypercapnic conditions for 1 hour following administration of said dose of (R)-dihydroetorphine intravenously over 10 minutes.

27. The method as claimed in claim 23, wherein said method increases a pain threshold level in said subject relative to a baseline level pre-administration of (R)-dihydroetorphine by at least 1.2 times.

28. The method as claimed in claim 23, wherein the pain is nociceptive pain.

29. A method of providing pain relief in a human subject in need thereof comprising administering (R)-dihydroetorphine to said subject intravenously in a dose of 0.075 to 0.15 µg/kg, wherein said dose provides opioid-related respiratory depression of 65% or less relative to a baseline level pre-administration of (R)-dihydroetorphine and at least one of the following criteria is satisfied in 7.5 hours post administration of (R)-dihydroetorphine:
average NAS score for dizziness of 0 to 50,
average NAS score for euphoria of 0 to 60,
average NAS score for nausea of 0 to 40,
average NAS score for sedation of 0 to 60, or
average NAS score for dysphoria of 0 to 40.

30. The method as claimed in claim 29, wherein the level of respiratory depression in said subject provided by said dose is between 20 and 65% relative to the baseline level pre-administration of (R)-dihydroetorphine.

31. The method as claimed in claim 29, wherein said method increases a pain threshold level in said subject relative to a baseline level pre-administration of (R)-dihydroetorphine by at least 1.2 times.

32. The method as claimed in claim 29, wherein the pain is nociceptive pain.

* * * * *